United States Patent
Breaker et al.

(10) Patent No.: US 9,744,191 B2
(45) Date of Patent: Aug. 29, 2017

(54) ANTIMICROBIAL COMPOSITIONS AND METHODS

(71) Applicant: Yale University, New Haven, CT (US)

(72) Inventors: Ronald R. Breaker, Guilford, CT (US); Sanshu Li, New Haven, CT (US)

(73) Assignee: Yale University, New Haven, CT (US)

(*) Notice: Subject to any disclaimer, the term of this patent is extended or adjusted under 35 U.S.C. 154(b) by 0 days.

(21) Appl. No.: 14/384,106

(22) PCT Filed: Mar. 13, 2013

(86) PCT No.: PCT/US2013/030788
§ 371 (c)(1),
(2) Date: Sep. 9, 2014

(87) PCT Pub. No.: WO2013/142184
PCT Pub. Date: Sep. 26, 2013

(65) Prior Publication Data
US 2015/0030701 A1    Jan. 29, 2015

Related U.S. Application Data

(60) Provisional application No. 61/612,689, filed on Mar. 19, 2012.

(51) Int. Cl.
| | | |
|---|---|---|
| A61K 33/20 | (2006.01) | |
| A61K 33/16 | (2006.01) | |
| A61K 31/7048 | (2006.01) | |
| A61K 31/55 | (2006.01) | |
| A61K 45/06 | (2006.01) | |
| A61K 33/18 | (2006.01) | |
| A61K 33/00 | (2006.01) | |
| A61K 31/4196 | (2006.01) | |
| A61K 31/70 | (2006.01) | |
| A61K 33/14 | (2006.01) | |
| A61K 31/167 | (2006.01) | |
| A61K 31/381 | (2006.01) | |
| A61K 31/4427 | (2006.01) | |

(52) U.S. Cl.
CPC ............ *A61K 33/20* (2013.01); *A61K 31/167* (2013.01); *A61K 31/381* (2013.01); *A61K 31/4196* (2013.01); *A61K 31/4427* (2013.01); *A61K 31/55* (2013.01); *A61K 31/70* (2013.01); *A61K 31/7048* (2013.01); *A61K 33/00* (2013.01); *A61K 33/14* (2013.01); *A61K 33/16* (2013.01); *A61K 33/18* (2013.01); *A61K 45/06* (2013.01)

(58) Field of Classification Search
None
See application file for complete search history.

(56) References Cited

U.S. PATENT DOCUMENTS

| | | |
|---|---|---|
| 5,217,965 A | 6/1993 | Oshlack |
| 5,294,605 A | 3/1994 | Houghten |
| 5,470,950 A | 11/1995 | Maloy |
| 5,792,831 A | 8/1998 | Maloy |
| 5,847,047 A | 12/1998 | Haynie |
| 6,348,445 B1 | 2/2002 | Kari |
| 6,518,252 B2 | 2/2003 | Wooley |
| 6,800,727 B2 | 10/2004 | Hahm |
| 7,129,208 B2 | 10/2006 | Gokel |
| 7,563,764 B2 | 7/2009 | Lu |
| 7,847,059 B2 | 12/2010 | ONeil |

FOREIGN PATENT DOCUMENTS

| | | | | |
|---|---|---|---|---|
| EP | 0093373 A1 | * | 11/1983 | ........... A61K 9/0043 |
| EP | 0421733 | | 4/1995 | |
| EP | 1206930 | | 3/2004 | |
| GB | 1436306 A | * | 5/1976 | ............. A01N 37/22 |
| WO | 02069983 | | 9/2002 | |
| WO | 2007096137 | | 8/2007 | |

OTHER PUBLICATIONS

Zamos et al. (J. Am. Vet. Med. Assoc.,1996, 208, 100-101).*
Hall (J. Am. Vet. Med. Assoc.,1917, 494-497 and 500-501).*
Wijnker et al. (Food Microbiol., 2006, 23, 657-662).*
Hendricks (Antimicrobial Effects of selected Non-antibiotics on Sensitivity and Invasion of gram-positive bacteria, Ph.D. thesis, 2006, p. 24).*
Brown (in www.Drugs.com/forum/latest-drug-related-news/anti-fungus-drug-useful-sinus-problem-24751.html, article posted by Stingray, Feb. 2, 2005).*
Merck Veterinary Manual, Antifungals for Integumentary Disease, (http://www.merckvetmanual.com/mvm/pharmacology/systemic_pharmacotherapeutics_of_the_integumentary_system/antifungals_for_integumentary_disease.html, cached Google Feb. 22, 2006).*
Taintor, J. "Treatment of conidiobolomycosis with fluconazole in two pregnant mares" Journal of Veterinary Internal Medicine, 2004, 18, 363-364.*
Baker, et al., "Widespread genetic switches and toxicity resistance proteins for fluoride" , Science, 335(6065):223-5 (2012).
Bamford, et al., "Preclinical Toxicology of NP213, a Novel Fungicidal Peptide for the Treatment of Onychomycosis",ICAAC 49th Conference Proceedings, Poster Abstract F1-854(2009).
Christensen, et al., "Channel-forming properties of cecropins and related model compounds incorporated into planar lipid membranes" , PNAS, 85:5072-76 (1988).

(Continued)

*Primary Examiner* — Mina Haghighatian
*Assistant Examiner* — Erin Hirt
(74) *Attorney, Agent, or Firm* — Pabst Patent Group LLP

(57) ABSTRACT

Disclosed are compositions and methods for antimicrobial use. The compositions contain a small antimicrobial agent and a permeabilizing agent. The antimicrobial compositions can be antifungal or antibacterial compositions.

25 Claims, 10 Drawing Sheets

(56) References Cited

OTHER PUBLICATIONS

De Kruijff, et al., "Polyene antibiotic-sterol interactions in membranes of Acholeplasma laidlawii cells and lecithin liposomes. 3. Molecular structure of the polyene antibiotic-cholesterol complexes", Biochim. Biophys. Acta, 339:57-70 (1974).
Dismukes, "Antifungal therapy: lessons learned over the past 27 years", Clin. Infect. Disease, 42:1289-96 (2006).
Duncan, et al., "In Vitro & Ex Vivo Activity of NP213, a Fungicidal Peptide for the Treatment of Onychomycosis", ICAAC 49th Conference Proceedings, Poster Abstract F1-852(2009).
Finn, et al., "The Pfam protein families database", Nucleic Acids Res., 38:D211-22 (2010).
Flisfisch, et al., "Effects of fluorides on Candida albicans", Oral Dis., 14:296-301 (2008).
Ghannoum and Rice, "Antifungal agents: mode of action, mechanisms of resistance, and correlation of these mechanisms with bacterial resistance", Clin. Microbiol. Rev., 12(4):501-17 (1999).
Hector, "Compounds active against cell walls of medically important fungi", Clin. Rev. Microbiol., 6:1-21 (1993).
Holz, "The effects of the polyene antibiotics nystatin and amphotericin B on thin lipid membranes", Ann. N. Y. Acad. Sci., 235:469-79 (1974).
Kaur and Kakkar, "Topical delivery of antifungal agents", Expert Opin. Drug Deliv., 7(11):1303-27 (2010).
Leslie, et al., "Growth of Verticillium lecanil on medium containing sodium fluoride", Trans. British Mycol. Soc., 58:351-2•(1972).
Li and Breaker, et al., "Floride enhances the activity of fungicides that destabilize cell membrances", Bioorgan Medicinal Chem Ltrs., 22(9):3317-22 (2012).
Mandal and Breaker, "Gene regulation by riboswitches", Nat Rev. Mol. Cell Biol., 5:451-63(2004).
Nickerson, et al., "Reversal of Fluoride Inhibition of Yeast Growth with Glucose-1-Phosphate", Am. J. Botany., 39:669-79 (1952).
Pitman, et al., "Addressing current medical needs in invasive fungal infection prevention and treatment with new antifungal agents, strategies and formulations", Expert Opin. Emerg. Drugs, 16:559-86 (2011).
Rapp, et al., "Identification and evolution of dual-topology membrane proteins", Nat. Struct. Mol. Biol., 13:112-6 (2006).
Roth and Breaker, "The structural and functional diversity of metabolite-binding riboswitches", Annu. Rev. Biochem., 78:305-34 (2009).
Smith, et al., "Riboswitch RNAs: regulation of gene expression by direct monitoring of a physiological signal", RNA Biol., 7:104-10 (2010).
Treshow, "Response of some pathogenic fungi to sodium fluoride", Mycologia., 57:216-21 (1965).
Weinberg, et al., "Comparative genomics reveals 104 candidate structured RNAs from bacteria, archaea, and their metagenomes", Genome Biol., 11:R31 (2010).

* cited by examiner

ANTIMICROBIAL COMPOSITIONS AND METHODS

CROSS-REFERENCE TO RELATED APPLICATIONS

This application is a §371 application of the International Application No. PCT/US2013/030788, filed in the United States Receiving Office for the PCT on Mar. 13, 2013, which claims the benefit of and priority to U.S. Provisional Application No. 61/612,689, filed Mar. 19, 2012, entitled "Antimicrobial Compositions and Methods", the disclosure of which is hereby incorporated herein by reference in its entirety.

STATEMENT REGARDING FEDERALLY SPONSORED RESEARCH OR DEVELOPMENT

This invention was made with Government Support under Agreement GM022778 awarded by the National Institutes of Health (NIH). The Government has certain rights in the invention.

FIELD

Described herein are compositions and methods for delivering antimicrobial agents to cells and subjects.

BACKGROUND

A recent discovery showed a fluoride-responsive riboswitch class (Weinberg, Z., et al., Genome Biol. 2010, 11, R31; Baker, J. L., et al., Science 2011) present in many bacterial and archaeal species. Riboswitches are metabolite- or ion-sensing domains found within the noncoding portions of certain messenger RNAs where they control the expression of adjoining protein coding regions (Mandal, M. et al., Nature Rev. Mol. Cell Biol. 2004, 5, 451; Roth, A. et al., Annu. Rev. Biochem. 2009, 78, 305; Smith, A. M. et al., RNA Biol. 2010, 7, 104-110). Members of the fluoride riboswitch class bind fluoride anions and regulate numerous genes whose protein products appear to overcome the inherent toxicity of this anion (Baker, J. L., et al., Science 2011).

Although fungi lack representatives of the known fluoride riboswitch class, many fungal species carry a homolog of the gene most commonly associated with fluoride riboswitches in bacteria. This gene (called crcB) codes for a member of a family of proteins predicted to be membrane-associated transporters (Rapp, M. et al., Nat. Struct. Mol. Biol. 2006, 13, 112; Finn, R. D. et al., Nucleic Acids Res. 2010, 38, D211; Holt, R. J. Ann. N. Y. Acad. Sci. 1974, 235, 469). A genetic knock-out of crcB in the bacterium *Escherichia coli* results in a strain that is approximately 200-fold more sensitive to fluoride, and these cells accumulate higher cytoplasmic concentrations of fluoride compared to wild-type cells when grown in identical fluoride-supplemented growth media (Baker, J. L., et al., Science 2011). Thus, compositions enhancing the toxicity of fluoride are desirable.

Antimicrobial compounds and compositions are well known in the art. Humans can be infected with a diversity of fungal and bacterial species and the outcomes of these diseases can range from minor discomfort and disfiguration to death. Numerous antifungal therapies have been developed over the last several decades that have been very effective (Dismukes, W. E. Clin. Infect. Disease 2006, 42, 1289; Pitman, S. et al., Expert Opin. Emerg. Drugs 2011, 16, 559), but many challenges still exist when treating fungal infections, including the emergence of drug resistance (Ghannoum, M. A.; Rice, L. B. Clin. Microbiol. Rev. 1999, p. 501). Fungal infections on the surface of the body are among the most common (Kaur, I. P.; et al., Expert Opin. Drug Deliv. 2010, 7, 1303) and usually can be overcome by topical treatment with antifungal agents, although poor efficacy can sometimes limit the utility of existing compounds. Fluoride has long been known to inhibit bacterial and fungal cell growth by blocking the functions of key metabolic enzymes. However, a high concentration of fluoride typically is required to provide effective antimicrobial properties.

Other antimicrobial compounds disrupt the integrity of cell membranes which leakage of a variety of small molecules such as potassium and other ion and solute components out of the cell. This disruption in membrane integrity ultimately leads to cell death. One class of such compounds is polyene macrolide antibiotics that selectively inhibit organisms whose membranes contain certain sterols. Their mechanism of action is, at least in part, dependent upon their binding to a sterol moiety, primarily ergosterol, present in the membrane of sensitive fungi. Once this interaction occurs, the polyenes form pores or channels in the fungal cell membrane which results in an increase of permeability of the membrane (WO/2007/096137). Polyene macrolide antifungal agents, such as amphotericin B and nystatin, are well known in the art for the treatment of fungal infections. However, when administered parenterally, such polyene macrolide antifungal agents have a number of serious side effects including nephrotoxicity. These side effects limit the amount of the polyene macrolide antifungal agent that can be administered safely (even topically) to a patient and thus, such side effects limit the effectiveness of these antifungal agents.

Thus, a need exists for new methods and compositions that enhance the efficacy of such antimicrobial compositions thereby permitting a reduced amount of antimicrobial agents to be administered.

SUMMARY

Disclosed herein are antimicrobial compositions having a therapeutically effective amount of a small antimicrobial agent and a permeabilizing agent. In one embodiment, the small antimicrobial agent can be a small antifungal agent. In one embodiment, the small antimicrobial agent can be an anion or a pharmaceutically acceptable salt thereof. In one embodiment, the small antimicrobial agent can be selected from the group consisting of fluoride, chloride, bromide and iodine. In one embodiment, the small antimicrobial agent can be selected from the group consisting of fluoride salts, chloride salts, bromide salts and iodine salts. In one embodiment, the small antimicrobial agent can be fluoride or a salt thereof. In one embodiment, the permeabilizing agent is an antifungal agent. In one embodiment, if the small antimicrobial agent is a small antifungal agent, the permeabilizing agent is not a small antifungal agent. In one embodiment, the permeabilizing agent can be a polyene or Novexatin®. In one embodiment, the polyene can be selected from the group consisting of amphotericin B, amphotericin B deoxycholate, liposomal amphotericin B, amphotericin B lipid complex, amphotec candidin, candidoin, candidinin, mycoheptin, nystatin, polyfungin, aureofacin, vacidin, trichomycin, candicidin and pimaricin. In one embodiment, the polyene can be amphotericin B. In one embodiment, the permeabilizing agent can be a transporter inhibitor. In one embodiment, the permeabilizing agent can be a tricyclic antidepressant. In one embodiment, the permeabilizing agent can be imipramine. In one embodiment, the permeabilizing agent can be a selective serotonin reuptake inhibitor. In one embodiment, the permeabilizing agent is an amphiphilic peptide. In one embodiment, amphiphilic peptides can be excluded as the permeabilizing agent. In one embodiment, the permeabilizing agent is a peptide. In one embodiment, peptides can be excluded as the permeabilizing agent. In one embodiment, the permeabilizing agent can be an ion channel-forming peptide or protein. In one embodiment, ion channel-forming peptides and proteins can be excluded as the permeabilizing agent.

Also disclosed herein are methods of treating a microbial condition, the method including administering to a subject a therapeutically effective amount of a small antimicrobial agent and a permeabilizing agent. In one embodiment, the small antimicrobial agent can be an antifungal agent. In one embodiment, the small antimicrobial agent can be an anion or a pharmaceutically acceptable salt thereof. In one embodiment, the small antimicrobial agent can be selected from the group consisting of fluoride, chloride, bromide and iodine. In one embodiment, the small antimicrobial agent can be selected from the group consisting of fluoride salts, chloride salts, bromide salts and iodine salts. In one embodiment, the small antimicrobial agent can be fluoride or a salt thereof. In one embodiment, the permeabilizing agent can be an antifungal agent. In one embodiment, the permeabilizing agent can be a polyene. In one embodiment, the polyene can be selected from the group consisting of amphotericin B, amphotericin B deoxycholate, liposomal amphotericin B, amphotericin B lipid complex, amphotec, candidin, candidoin, candidinin, mycoheptin, nystatin, polyfungin, aureofacin, vacidin, trichomycin, candicidin and pimaricin. In one embodiment, the polyene can be amphotericin B. In one embodiment, the permeabilizing agent can be a transporter inhibitor. In one embodiment, the permeabilizing agent can be a tricyclic antidepressant. In one embodiment, the permeabilizing agent can be imipramine. In one embodiment, the permeabilizing agent can be a selective serotonin reuptake inhibitor. In one embodiment, the permeabilizing agent is an amphiphilic peptide. In one embodiment, amphiphilic peptides can be excluded as the permeabilizing agent. In one embodiment, the permeabilizing agent is a peptide. In one embodiment, peptides can be excluded as the permeabilizing agent. In one embodiment, the permeabilizing agent can be an ion channel-forming peptide or protein. In one embodiment, ion channel-forming peptides and proteins can be excluded as the permeabilizing agent.

Disclosed herein are antimicrobial agents that disrupt cell membrane integrity exhibit improved ability to inhibit cell growth when used with low concentrations, such as millimolar concentrations, of small antimicrobial agents, such as fluoride. The results disclosed herein show that permeabilizing agents can increase the cellular uptake of a small antimicrobial agent, such as fluoride. The compositions and methods disclosed herein provide new opportunities for creating antimicrobial compounds whose functions are enhanced when combined with otherwise sub-inhibitory concentrations of small ions.

Additional advantages of the disclosed method and compositions will be set forth in part in the description which follows, and in part will be understood from the description, or may be learned by practice of the disclosed method and compositions. The advantages of the disclosed method and compositions will be realized and attained by means of the elements and combinations particularly pointed out in the appended claims. It is to be understood that both the foregoing general description and the following detailed description are exemplary and explanatory only and are not restrictive of the invention as claimed.

BRIEF DESCRIPTION OF THE DRAWINGS

The accompanying drawings, which are incorporated in and constitute a part of this specification, illustrate several embodiments of the disclosed method and compositions and together with the description, serve to explain the principles of the disclosed method and compositions.

DETAILED DESCRIPTION

Figure 1A:
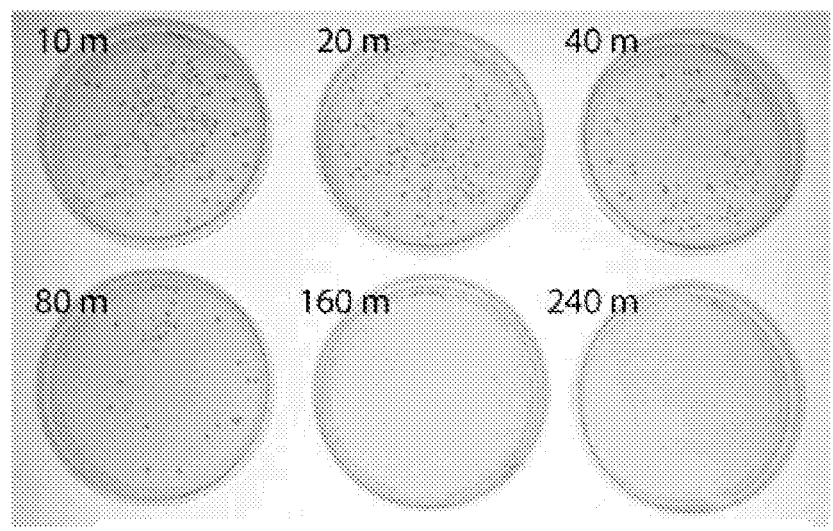
FIG. 1. (A) Demonstration that high fluoride concentration in *S. cereviciae* culture causes loss of cell viability. Cells were cultured in liquid medium in the presence of 300 mM fluoride for the times (in minutes) indicated and then plated on solid medium in the absence of added fluoride. Plate images were recorded after extended incubation and colonies were counted. See Supplementary data for all methods details. (B) Plots of the numbers of colonies present versus incubation time as noted in A.

The disclosed method and compositions may be understood more readily by reference to the following detailed description of particular embodiments and the Example included therein and to the Figures and their previous and following description.

1. Definitions

As used herein, the terms "effective amount" or "therapeutically effective amount" or the like terms refer to an amount of a small antimicrobial agent and a permeabilizing agent required to affect a disease in the extent, amount or rate of spread of a microbial condition, such as bacterial or fungal, when administered to a subject.

As used herein, the term "effective reduced amount" or like terms refer to an amount of a small antimicrobial agents that is less than its minimum inhibitory concentration (MIC) when used in the absence of a permeabilizing agent but that is an effective amount when used with a permeabilizing agent. Similarly, an effective reduced amount of a permeabilizing agent is an amount of a permeabilizing agent that is less than its MIC when used in the absence of a small antimicrobial agent but that is an effective amount when used with a small antimicrobial agent. The disclosed compositions preferably is an effective reduced amount of the antimicrobial agent, the permeabilizing agent, or both.

As used herein, the term "first antimicrobial agent" or the like terms refer to an antimicrobial agent that is not a permeabilizing agent.

As used herein, the term "permeabilizing agent" or the like terms refer to agents that destabilize or disrupt the integrity of cell membranes. Disrupting the integrity of cell membranes provides, for example, the formation of channels and pores in the cell membrane.

As used herein, the term "small antimicrobial agent" or the like terms refer to an antimicrobial agent that more effectively provides antimicrobial properties once the integrity of cell membranes has been disrupted or destabilized. For example, the formation of pores and channels in a disrupted cell membrane can allow small antimicrobial agents to more easily enter the cell to provide its antimicrobial properties.

The term "subject" or "patient" refers to any individual who is the target of administration. The subject can be a vertebrate, for example, a mammal Thus, the subject can be a human. The subject can be domesticated, agricultural, or zoo- or circus-maintained animals. Domesticated animals include, for example, dogs, cats, rabbits, ferrets, guinea pigs, hamsters, pigs, monkeys or other primates, and gerbils. Agricultural animals include, for example, horses, mules, donkeys, burros, cattle, cows, pigs, sheep, and alligators. Zoo- or circus-maintained animals include, for example, lions, tigers, bears, camels, giraffes, hippopotamuses, and rhinoceroses. The term does not denote a particular age or sex.

By "treatment" and "treating" is meant the medical management of a subject with the intent to cure, ameliorate, stabilize, or prevent a disease, pathological condition, or disorder. This term includes active treatment, that is, treatment directed specifically toward the improvement of a disease, pathological condition, or disorder, and also includes causal treatment, that is, treatment directed toward removal of the cause of the associated disease, pathological condition, or disorder. In addition, this term includes palliative treatment, that is, treatment designed for the relief of symptoms rather than the curing of the disease, pathological condition, or disorder; preventative treatment, that is, treatment directed to minimizing or partially or completely inhibiting the development of the associated disease, pathological condition, or disorder; and supportive treatment, that is, treatment employed to supplement another specific therapy directed toward the improvement of the associated disease, pathological condition, or disorder. It is understood that treatment, while intended to cure, ameliorate, stabilize, or prevent a disease, pathological condition, or disorder, need not actually result in the cure, ameliorization, stabilization or prevention. The effects of treatment can be measured or assessed as described herein and as known in the art as is suitable for the disease, pathological condition, or disorder involved. Such measurements and assessments can be made in qualitative and/or quantitative terms. Thus, for example, characteristics or features of a disease, pathological condition, or disorder and/or symptoms of a disease, pathological condition, or disorder can be reduced to any effect or to any amount.

The term "amphiphilic peptide" refers to peptides that are amphiphilic. A peptide is amphiphilic when the peptide can form monolayers, vesicles, micelles, bilayers, liposomes, and the like when in aqueous environments.

The term "ion channel-forming peptide or protein" refers to a peptide or protein that increases the permeability for ions across a natural or synthetic lipid membrane. B. Christensen et al. PNAS vol. 85 P. 5072-76 (July 1988) describes methodology which indicates whether or not a peptide or protein has ion channel-forming properties and is therefore an ionophore. As used herein an ion channel-forming peptide or ion channel forming protein is a peptide or protein which has ion channel-forming properties as determined by the method of Christensen et al.

2. Antimicrobial Compositions

Described herein are antimicrobial compositions. The antimicrobial compositions can treat any microbial condition. In one embodiment, the microbial condition arises from pathogens or organisms with cell membranes that contain a sterol moiety. In one embodiment, the microbial condition can be a fungal disease. In one embodiment, the microbial condition can be a bacterial condition. In one embodiment, the fungal disease can be a disease re-suiting from *Candida* infections (e.g., *C. albicans, C. tropicalis*, etc.) as well as a variety of other diseases such as histoplasmosis, coccidioidomycosis, systemic sporotrichosis, aspergillosis, mucormycosis, chromablastomycosis, blastomycosis and cryptococcosis.

In one embodiment, the antimicrobial compositions can be antifungal compositions. In one embodiment, the antimicrobial compositions can be antibacterial compositions. In one embodiment, the antimicrobial compositions can be antifungal and antibacterial compositions. In one embodiment, the antimicrobial compositions can include a small antimicrobial agent and a permeabilizing agent. In one embodiment, the antimicrobial compositions can include a small antimicrobial agent, a permeabilizing agent and a first antimicrobial agent. In one embodiment, the small antimicrobial agent and the permeabilizing agent can have a synergistic effect.

i. Small Antimicrobial Agents

In one embodiment, a small antimicrobial agent can be present in the composition in a therapeutically effective amount. In one embodiment, a small antimicrobial agent can be a small antifungal agent. In one embodiment, a small antimicrobial agent can be a small antibacterial agent. In one embodiment, a small antimicrobial agent can be a small antibacterial agent and a small antifungal agent.

In one embodiment, a small antimicrobial agent can work in synergy with a permeabilizing agent. For example, a small antimicrobial agent can provide antimicrobial properties at a lower concentration or amount when added, combined or administered with a permeabilizing agent than when administered alone or in combination with other non-permeabilizing agents. For example, the minimum inhibitory concentration (MIC) can be lower for a small antimicrobial agent when added, combined or administered with a permeabilizing agent. In one embodiment, less amount of a small antimicrobial agent is needed to be considered a "therapeutically effective amount" when added, combined or administered with a permeabilizing agent. In one embodiment, the MIC of a small antimicrobial agent can be improved 400 fold, 300 fold, 200 fold, 100 fold, 80 fold, 60 fold, 50 fold, 40 fold, 30 fold, 25 fold, 20 fold, 15 fold, 14 fold, 13 fold, 12 fold, 11 fold, 10 fold, 9 fold, 8 fold, 7 fold, 6 fold, 5 fold, 4 fold, 3 fold or 2 fold when administered with a permeabilizing agent.

In one embodiment, a small antimicrobial agent can penetrate a destabilized or disputed cell membrane. In one embodiment, a small antimicrobial agent can penetrate a destabilized or disputed cell membrane though the pore and channels the destabilized or disputed cell membrane. In one embodiment, the small antimicrobial agent can be an organic molecule or atom. In one embodiment, the small antimicrobial agent can be an inorganic molecule or atom. In one embodiment, a small antimicrobial agent can be an anion. In one embodiment, a small antimicrobial agent can be a halogen anion.

Fluoride and other halogen anions are small chemical entities. For example, fluoride provides antifungal activity. Permeabilizing agents that disrupt the integrity of cell membranes interact synergistically with small antimicrobial agents, such as fluoride to more effectively inhibit fungal growth. Specifically, the addition of fluoride to a fungal growth medium containing a concentration of such an antifungal agent below its typical MIC (minimum inhibitory concentration) improves its MIC value. Likewise, permeabilizing agents lower the concentration of small antimicrobial agents, such as fluoride, needed to inhibit fungal growth. In one embodiment, a small antimicrobial agent can be fluoride, chloride, bromide or iodine. In one embodiment, a small antimicrobial agent can be fluoride.

In one embodiment, the small antimicrobial agent can be added to the composition in its corresponding salt form. For example, the small antimicrobial agent can be added to the composition as NaF, NaCl, KF, KCl, NaI or M. In one embodiment, the small antimicrobial agent can be added to the composition as NaF.

ii. Permeabilizing Agents

Among the existing antimicrobial compound classes, such as antifungal compounds, are examples that are known or predicted to selectively disrupt the integrity of fungal membranes. In particular, members of the polyene class form multimer complexes in fungal membranes (De Kruijff, B. et al., Biochim. Biophys. Acta 1974, 339, 57; Kerridge, D. In: The Eukaryotic Cell; Cambridge University Press, 1980, p. 103) resulting in pores that permit leakage of cytoplasmic constituents (Hector, R. F. Clin. Rev. Microbiol. 1993, 6, 1). The flow of small molecules and ions is not unidirectional, therefore, compounds, such as small antimicrobial agents can equilibrate with the interiors of cells whose membranes have been compromised by the fungicide, i.e. permeabilizing agent.

In one embodiment, a permeabilizing agent can be present in the composition in a therapeutically effective amount. In one embodiment, a permeabilizing agent can be an antifungal agent. In one embodiment, a permeabilizing agent can be an antibacterial agent. In one embodiment, a permeabilizing agent can be an antibacterial agent and an antifungal agent.

In one embodiment, a permeabilizing agent can work in synergy with a small antimicrobial agent. For example, a permeabilizing agent can provide antimicrobial properties at a lower concentration or amount when added, combined or administered with a small antimicrobial agent than when administered alone or in combination with other non-small antimicrobial agents. For example, the MIC can be lower for a permeabilizing agent when added, combined or administered with a small antimicrobial agent. In one embodiment, less amount of a permeabilizing agent is needed to be considered a "therapeutically effective amount" when added, combined or administered with a small antimicrobial agent. In one embodiment, the MIC of a permeabilizing agent can be improved 400 fold, 300 fold, 200 fold, 100 fold, 80 fold, 60 fold, 50 fold, 40 fold, 30 fold, 25 fold, 20 fold, 15 fold, 14 fold, 13 fold, 12 fold, 11 fold, 10 fold, 9 fold, 8 fold, 7 fold, 6 fold, 5 fold, 4 fold, 3 fold or 2 fold when administered with a small antimicrobial agent.

a. Polyenes

In one embodiment, the permeabilizing agent can be a polyene. Polyenes are effective antifungal agents due to their potent fungicidal activity, broad spectrum, and relatively low frequency of resistance among the fungal pathogens. It has been shown that the polyenes have selectivity for inhibiting organisms whose membranes contain sterols. Their mechanism of action is, at least in part, dependent upon their binding to a sterol moiety, primarily ergosterol, present in the membrane of sensitive fungi. Once this interaction occurs, the polyenes form pores or channels in the fungal cell membrane which results in an increase of permeability of the membrane and the leakage of a variety of small molecules such as potassium and other ion and solute components out of the cell (WO/2007/096137). This disruption in membrane integrity ultimately leads to cell death. The polyenes are commercially available or can be conventionally prepared by techniques known to one of skill in the art. For example, representative patents describing various polyenes and derivatives thereof, as well as the synthesis and preparation thereof, include U.S. Pat. Nos.

2,797,183; 2,908,611; 4,812,312; 5,567,685; 5,606,038; 5,908,834; 5,965,158; 6,080,744; 6,121,244; and 6,413,537.

In one embodiment, the polyene can be selected from the group consisting of amphotericin B, amphotericin B deoxycholate, liposomal amphotericin B, amphotericin B lipid complex, amphotec, candidin, candidoin, candidinin, mycoheptin, nystatin, polyfungin, aureofacin, vacidin, trichomycin, candicidin and pimaricin. In one embodiment, the polyene can be amphotericin B or nystatin. In one embodiment, the polyene can be amphotericin B.

b. Novetaxin®

In one embodiment, the permeabilizing agent can be Novetaxin® or a derivative thereof. Novetaxin® is a circular hepta-arginine peptide with the commercial name Novexatin® (NP213; NovaBiotics, Aberdeen, UK) (O'Neil, D. U.S. Pat. No. 7,847,059 B2, 2010; Duncan, V. M. S. et al., ICAAC 49th Conference Proceedings, 2009, Poster Abstract F1-852; Bamford, C. A. et al., ICAAC 49th Conference Proceedings, 2009, Poster Abstract F1-854).

c. Amphiphilic Peptides

Useful permeabilizing agents include amphiphilic peptides. The term "amphiphilic peptide" refers to a peptide with spatially segregated polar and non-polar residues. Examples include amphiphilic peptides described in U.S. Pat. Nos. 5,217,965, 5,294,605, 5,470,950, 5,792,831, 5,847,047, 6,348,445, 6,800,727, 7,129,208, and 7,563,764, which are hereby incorporated by reference in their entirety and specifically for their description of amphiphilic peptides.

iii. First Antimicrobial Agents

In one embodiment, the first antimicrobial agent can be a small antimicrobial agent. In one embodiment, the first antimicrobial agent can work in synergy with a small antimicrobial agent. For example, a first antimicrobial agent can inhibit fluoride transporters in a cell and works in synergy when fluoride is the small antimicrobial agent. Fluoride transporters are membrane proteins that facilitate passage of fluoride ions through the membrane. Fluoride transporters have been discovered in, for example, a variety of bacteria, archae, and fungi. Fluoride transporters can be used, for example, to increase the fluoride tolerance of a cell or as a target for inhibitors that can increase the level of fluoride in a cell. The fluoride transporters can be a bacterial fluoride transporter, an archaeal fluoride transporter or a eukaryotic fluoride transporter. The eukaryotic fluoride transporters can be, but are not limited to, a fungal fluoride transporter, a plant fluoride transporter, or other eukaryotic species transporter.

As used herein, "transporter" refers to a protein that facilitates passage of compounds or molecules through a lipid membrane. For example, transporters can facilitate passage of compounds and molecules through cell membranes. Transporters can be indiscriminate or non-selective or transporters can be fastidious or selective. That is, non-selective transporters can facilitate passage of a range of compounds or molecules—a particular class of compound or molecule, for example—and selective transporters can selectively facilitate only one compound or molecule or type of compound or molecule—a single compound, for example. The disclosed fluoride transporters generally are selective transporters that do not significantly facilitate passage of ions, elements, or compounds other than fluoride. Transporters can facilitate passage of by a variety of mechanisms, such as passive transport, active transport, pumping, etc. Transporters can be referred to with various terms, such as pumps, channels, gates, pores, etc., some of which are meant to indicate their mechanism. A native fluoride transporter refers to a fluoride transporter that naturally occurs in a cell, tissue, organ, organism, microorganism, etc.

Fluoride transporters have been identified as a subset of proteins associated with chloride transporters. For example, some fluoride transporters are encoded by $eriC^F$ genes and others by crcB genes. The protein sequence of EriC fluoride transporters were aligned to one another. The alignment included both proteins whose expression are regulated by a fluoride riboswitch as well as proteins that are not know to be regulated by a riboswitch. Proteins within version 44 of the RefSeq nucleotide database were used to form the alignment. The resulting multiple-sequence alignment defines the features of EriC proteins that function as fluoride channels. CrcB proteins can function as fluoride transporters or channels. To classify proteins as CrcB, the Pfam database (at internet site pfam.sanger.ac.uk) protein family with accession PF02537 was used in version 24.0 of the database. The Pfam database defines a protocol and parameters for determining whether a protein belongs to the CrcB class. In one embodiment, a first antimicrobial agent can inhibit a protein that acts as a fluoride transporter in a cell. In one embodiment, a first antimicrobial agent can inhibit crcB proteins. In some forms, the first antimicrobial agent has the structure

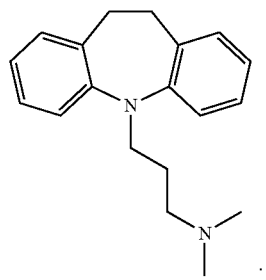 [SMILES: CN(C)CCCN1c2ccccc2CCc2ccccc21]

In one embodiment, a first antimicrobial agent can bind to small antimicrobial agent, such as fluoride, and that facilitates passage of fluoride through a cell membrane to fluoride. In some forms, the first antimicrobial agent has the structure

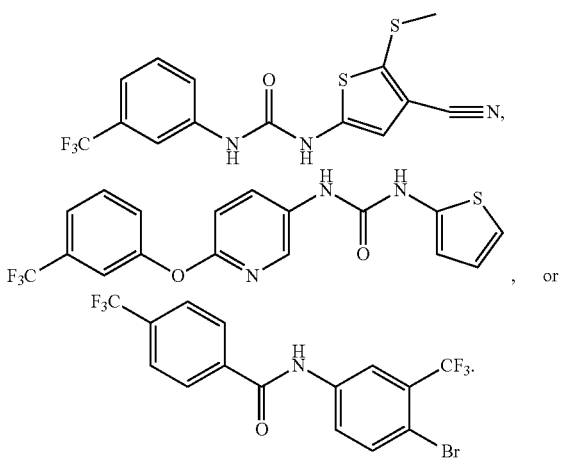

, or a. Transporter Inhibitors

Transporter inhibitors work as first antimicrobial agents by inhibiting transport of the antimicrobial agent out of cells.

For example, compounds that inhibit fluoride transporters can be used with fluoride in the disclosed compositions and methods to increase the cellular concentration of fluoride. It has been discovered that compounds used to reduce uptake of neurotransmitters (and related compounds) can inhibit transporters of small antimicrobial agents in microbial cells. Thus, one class of compounds useful as transporter inhibitors are compounds used to reduce uptake of neurotransmitters (and related compounds). Examples include antidepressants, aniolytics, stimulants, and anoretics. More specific examples include tricyclic antidepressant compounds (and related compounds), selective serotonin reuptake inhibitors (SSRIs) (and related compounds), norepinephrine reuptake inhibitors (and related compounds), dopamine reuptake inhibitors (and related compounds), adenosine reuptake inhibitors (and related compounds), endocannabinoid reuptake inhibitors (and related compounds), glutamate reuptake inhibitors (and related compounds), GABA reuptake inhibitors (and related compounds), glycine reuptake inhibitors (and related compounds), serotonin-norepinephrine reuptake inhibitors (and related compounds), norepinephrine-dopamine reuptake inhibitors (and related compounds), serotonin-dopamine reuptake inhibitors (and related compounds), serotonin-norepinephrine-dopamine reuptake inhibitors (and related compounds), serotonin-norepinephrine-dopamine-GABA-glycine reuptake inhibitors (and related compounds), Adrenergic reuptake inhibitor (ARI) (and related compounds), and excitatory amino acid reuptake inhibitor (EAARI) (and related compounds).

Examples of specific compounds include Dilazep (Cormelian), dipyridamole (Persantine), hexobendine (Ustimon), pentoxifylline (Trental), Amfonelic acid (AFA; WIN 25,978), benocyclidine (BTCP; GK-13), RTI-121, RTI-229, troparil (β-CPT; WIN 35,065-2), vanoxerine (GBR-12,909), AM-404, LY-2183240, O-2093, OMDM-2, UCM-707, VDM-11, Dihydrokainic acid, PDC, WAY-213,613, Deramciclane (EGIS-3886), nipecotic acid, tiagabine (Gabitril), ACPPB, ALX-5407, glycyldodecylamide, Org 24589, Org 25935, sarcosine, SSR-103,800, SSR-504,734, Atomoxetine (Strattera), nisoxetine (LY-94,939), reboxetine (Edronax, Vestra), viloxazine (Vivalan), Escitalopram (Lexapro, Cipralex), fluoxetine (Prozac), sertraline (Zoloft, Lustral), Desvenlafaxine (Pristiq), duloxetine (Cymbalta), milnacipran (Dalcipran, Ixel, Savella), venlafaxine (Effexor), Aminepine (Survector), bupropion (Wellbutrin, Zyban), methylenedioxypyrovalerone, methylphenidate (Ritalin, Concerta), pipradrol (Meretran), RTI-83, Cocaine, indatraline (Lu-19-005), nefopam (Acupan), tesofensine (NS-2330), Adhyperforin, and hyperforin.

Examples of serotonin reuptake inhibitors include selective serotonin reuptake inhibitors (SSRIs) such as citalopram (Celexa), dapoxetine (Priligy), escitalopram (Lexapro, Cipralex), femoxetine (Malexil), fluoxetine (Prozac), fluvoxamine (Luvox), indalpine (Upstene), paroxetine (Paxil, Seroxat), sertraline (Zoloft, Lustral), and zimelidine (Normud, Zelmid); serotonin-norepinephrine reuptake inhibitors (SNRIs) such as desvenlafaxine (Pristiq), duloxetine (Cymbalta), milnacipran (Ixel, Savella), and venlafaxine (Effexor); tricyclic antidepressants (TCAs) such as amitriptyline (Elavil), butriptyline (Evadyne), clomipramine (Anafranil), dibenzepin (Noveril), dosulepin (Prothiade), doxepin (Adapin, Sinequan), imipramine (Tofranil), lofepramine (Lomont, Gamanil), nortriptyline (Pamelor, Aventyl), protriptyline (Vivactil), and trimipramine (Surmontil); tetracyclic antidepressants (TeCAs) such as amoxapine (Asendin); opioid analgesics such as meperidine/pethidine (Demerol), methadone (Dolophine, Methadose), and propoxyphene (Darvon); first-generation antihistamines such as chlorpheniramine (Chlor-Trimeton, etc.), diphenhydramine (Benadryl, etc.), mepyramine/pyrilamine (Anthisan, etc.), and tripelennamine (Pyribenzamine, etc.); and other agents such as adhyperforin (found in *Hypericum perforatum* (St. John's Wort)), alaproclate (GEA-654), bicifadine (DOV-220,075), brasofensine (NS-2214), bromantane (ADK-709), cyclobenzaprine (Flexeril), dextromethorphan (DXM; Robitussin, etc.), dextrorphanol (DXO) (an active metabolite of DXM), diclofensine (Ro-8-4650), DOV-102,677, DOV-21,947, DOV-216,303, hyperforin (found in *Hypericum perforatum* (St. John's Wort)), indatraline (Lu-19-005), litoxetine (SL-810,385), lubazodone (YM-992, YM-35,995), mesembrine (found in *Sceletium tortuosum* (Kanna)), nefazodone (Serzone), nefopam (Acupan), NS-2359 (GSK-372,475), SB-649,915, SEP-225,289, SEP-227,162, sibutramine (Meridia, Reductil), tametraline (CP-24,411), tesofensine (NS-2330), trazodone (Desyrel), vilazodone (EMD-68,843), viqualine (PK-5078), and ziprasidone (Geodon, Zeldox).

iv. Carriers

In some forms, the antimicrobial compositions can further comprise a carrier. In some forms, the carrier can comprise a cream, paste, fluid, coating, paint, spray, detergent, or a combination. In some forms, the carrier can comprise antimicrobial cream, antimicrobial paste, antimicrobial fluid, antimicrobial coating, antimicrobial paint, antimicrobial spray, antimicrobial detergent, antimicrobial soap, mouthwash, skinwash, nasal wash, toothpaste, toothwash, dish detergent, laundry detergent, dishwasher detergent, nasal spray, mouth spray, throat spray, skin spray, douche fluid, enema fluid, wound cleanser, wound covering, eyewash, shampoo, facial wash, facial cream, or facial soap. In some forms, the composition can be an additive for addition to food or a product. Every compound, component, composition, etc. described herein is intended to be and should be considered to be specifically disclosed herein. Further, every subgroup that can be identified herein is intended to be and should be considered to be specifically disclosed herein. As a result, it is specifically contemplated that any compound, composition, or component of a composition can be either specifically included for or excluded from use or included in or excluded from a list of compound, composition, components, etc. For example, as one option, a group of permeabilizing agents is contemplated where each agent is as describe herein but is not an ion channel-forming peptide or protein, an amphiphilic peptide, or a biologically active protein. For example, the classes and individual examples of ion channel-forming peptides and proteins, amphiphilic peptides, and biologically active proteins can be independently and specifically included or excluded from the compositions and methods disclosed herein.

It is to be understood that the disclosed method and compositions are not limited to specific synthetic methods, specific analytical techniques, or to particular reagents unless otherwise specified, and, as such, may vary. It is also to be understood that the terminology used herein is for the purpose of describing particular embodiments only and is not intended to be limiting.

3. Methods

Also disclosed herein are methods of treating a microbial condition, the method including administering to a subject a therapeutically effective amount of a small antimicrobial agent and a permeabilizing agent. In one embodiment, the subject is in need of treatment of a microbial condition. In one embodiment, the subject has been diagnosed with a microbial condition.

As used herein, a "microbial condition" is any infection, growth, presence of one or more microbes. In one embodiment, the microbial condition arises from pathogens or organisms with cell membranes that contain a sterol moiety. In one embodiment, the microbial condition is a fungal condition. In one embodiment, the microbial condition is a bacterial condition. In one embodiment, the fungal condition can be a disease re-suiting from *Candida* infections (e.g., *C. albicans, C. tropicalis*, etc.). In one embodiment, the fungal condition can be selected from the group consisting of histoplasmosis, coccidioidomycosis, systemic sporotrichosis, aspergillosis, mucormycosis, chromablastomycosis, blastomycosis and cryptococcis. Also disclosed herein is a method including contacting a composition including a small antimicrobial agents and a permeabilizing agent with a cell. In one embodiment, the cell membranes of the cell contain a sterol moiety. In one embodiment, the cell is a fungal cell. In one embodiment, the cell is a bacterial cell. For example, the disclosed compositions can be used to inhibit, kill eliminate, and/or prevent microbial growth or presence in any environment, place, object, etc. For example, the disclosed compositions can be used to clean, wash, disinfect, etc. surfaces, objects, etc. As another example, the disclosed compositions can be used to prophylactically protect surfaces, environments, objects, etc. from microbial growth, presence, infection, etc. For example, the disclosed compositions can be used as a preservative to inhibit or prevent microbial growth in liquids, gels, viscous mixtures, foods, toothpaste, etc. In some forms, the disclosed compositions can be used in antimicrobial cream, antimicrobial paste, antimicrobial fluid, antimicrobial coating, antimicrobial paint, antimicrobial spray, antimicrobial detergent, antimicrobial soap, mouthwash, skinwash, nasal wash, toothpaste, toothwash, dish detergent, laundry detergent, dishwasher detergent, nasal spray, mouth spray, throat spray, skin spray, douche fluid, enema fluid, wound cleanser, wound covering, eyewash, shampoo, facial wash, facial cream, or facial soap. In some forms, the composition can be an additive for addition to food or a product. In some forms, the composition can be included in building materials. In some forms, the composition can be included in household objects and surfaces. The disclosed compounds and compositions can be included in any compositions, products, objects, foods, substances, etc.

Also disclosed are objects and substances comprising one or more of the disclosed compositions. In some forms, the composition can increase preservation of the object or substance. In some forms, the composition can reduce microbes on or in proximity to the object or substance.

4. Pharmaceutical and Other Compositions

The compositions and compounds disclosed herein can be administered in vivo in a pharmaceutically acceptable carrier. By "pharmaceutically acceptable" is meant a material that is not biologically or otherwise undesirable, i.e., the material may be administered to a subject without causing any undesirable biological effects or interacting in a deleterious manner with any of the other components of the pharmaceutical composition in which it is contained. The carrier would naturally be selected to minimize any degradation of the active ingredient and to minimize any adverse side effects in the subject, as would be well known to one of skill in the art.

The compositions or compounds disclosed herein can be administered orally, parenterally (e.g., intravenously), by intramuscular injection, by intraperitoneal injection, transdermally, extracorporeally, topically or the like, including topical intranasal administration or administration by inhalant. As used herein, "topical intranasal administration" means delivery of the compositions into the nose and nasal passages through one or both of the nares and can comprise delivery by a spraying mechanism or droplet mechanism, or through aerosolization of the nucleic acid or vector. Administration of the compositions by inhalant can be through the nose or mouth via delivery by a spraying or droplet mechanism. Delivery can also be directly to any area of the respiratory system (e.g., lungs) via intubation. The exact amount of the compositions required will vary from subject to subject, depending on the species, age, weight and general condition of the subject, the severity of the allergic disorder being treated, the particular nucleic acid or vector used, its mode of administration and the like. Thus, it is not possible to specify an exact amount for every composition. However, an appropriate amount can be determined by one of ordinary skill in the art using only routine experimentation given the teachings herein.

Parenteral administration of the composition or compounds, if used, is generally characterized by injection. Injectables can be prepared in conventional forms, either as liquid solutions or suspensions, solid forms suitable for solution of suspension in liquid prior to injection, or as emulsions. A more recently revised approach for parenteral administration involves use of a slow release or sustained release system such that a constant dosage is maintained.

The compositions and compounds disclosed herein can be used therapeutically in combination with a pharmaceutically acceptable carrier. Suitable carriers and their formulations are described in *Remington: The Science and Practice of Pharmacy* (21st ed.) ed. A. R. Gennaro, Mack Publishing Company, Easton, Pa. 2011. Typically, an appropriate amount of a pharmaceutically-acceptable salt is used in the formulation to render the formulation isotonic. Examples of the pharmaceutically-acceptable carrier include, but are not limited to, saline, Ringer's solution and dextrose solution. The pH of the solution is preferably from about 5 to about 8, and more preferably from about 7 to about 7.5. Further carriers include sustained release preparations such as semipermeable matrices of solid hydrophobic polymers containing the antibody, which matrices are in the form of shaped articles, e.g., films, liposomes or microparticles. It will be apparent to those persons skilled in the art that certain carriers may be more preferable depending upon, for instance, the route of administration and concentration of composition being administered.

Pharmaceutical carriers are known to those skilled in the art. These most typically would be standard carriers for administration of drugs to humans, including solutions such as sterile water, saline, and buffered solutions at physiological pH. The compositions can be administered intramuscularly or subcutaneously. Other compounds will be administered according to standard procedures used by those skilled in the art.

Pharmaceutical compositions may include carriers, thickeners, diluents, buffers, preservatives, surface active agents and the like in addition to the molecule of choice. Pharmaceutical compositions may also include one or more active ingredients such as antimicrobial agents, antiinflammatory agents, anesthetics, and the like.

The pharmaceutical composition may be administered in a number of ways depending on whether local or systemic treatment is desired, and on the area to be treated. Administration may be topically (including ophthalmically, vaginally, rectally, intranasally), orally, by inhalation, or parenterally, for example by intravenous drip, subcutaneous, intraperitoneal or intramuscular injection. The disclosed antibodies can be administered intravenously, intraperitoneally, intramuscularly, subcutaneously, intracavity, or transdermally.

Preparations for parenteral administration include sterile aqueous or non-aqueous solutions, suspensions, and emulsions. Examples of non-aqueous solvents are propylene glycol, polyethylene glycol, vegetable oils such as olive oil, and injectable organic esters such as ethyl oleate. Aqueous carriers include water, alcoholic/aqueous solutions, emulsions or suspensions, including saline and buffered media. Parenteral vehicles include sodium chloride solution, Ringer's dextrose, dextrose and sodium chloride, lactated Ringer's, or fixed oils. Intravenous vehicles include fluid and nutrient replenishers, electrolyte replenishers (such as those based on Ringer's dextrose), and the like. Preservatives and other additives may also be present such as, for example, antimicrobials, anti-oxidants, chelating agents, and inert gases and the like.

Formulations for topical administration may include ointments, lotions, creams, gels, drops, suppositories, sprays, liquids and powders. Conventional pharmaceutical carriers, aqueous, powder or oily bases, thickeners and the like may be necessary or desirable.

Compositions for oral administration include powders or granules, suspensions or solutions in water or non-aqueous media, capsules, sachets, or tablets. Thickeners, flavorings, diluents, emulsifiers, dispersing aids or binders may be desirable.

Some of the compositions may potentially be administered as a pharmaceutically acceptable acid- or base-addition salt, formed by reaction with inorganic acids such as hydrochloric acid, hydrobromic acid, perchloric acid, nitric acid, thiocyanic acid, sulfuric acid, and phosphoric acid, and organic acids such as formic acid, acetic acid, propionic acid, glycolic acid, lactic acid, pyruvic acid, oxalic acid, malonic acid, succinic acid, maleic acid, and fumaric acid, or by reaction with an inorganic base such as sodium hydroxide, ammonium hydroxide, potassium hydroxide, and organic bases such as mono-, di-, trialkyl and aryl amines and substituted ethanolamines.

Therapeutic compositions as disclosed herein may also be delivered by the use of monoclonal antibodies as individual carriers to which the compound molecules are coupled. The therapeutic compositions of the present disclosure may also be coupled with soluble polymers as targetable drug carriers. Such polymers can include, but are not limited to, polyvinylpyrrolidone, pyran copolymer, polyhydroxypropylmethacryl-amidephenol, polyhydroxyethylaspartamidephenol, or polyethyl-eneoxidepolylysine substituted with palmitoyl residues. Furthermore, the therapeutic compositions of the present disclosure may be coupled to a class of biodegradable polymers useful in achieving controlled release of a drug, for example, polylactic acid, polyepsilon caprolactone, polyhydroxy butyric acid, polyorthoesters, polyacetals, polydihydropyrans, polycyanoacrylates and cross-linked or amphipathic block copolymers of hydrogels.

Preferably at least about 3%, more preferably about 10%, more preferably about 20%, more preferably about 30%, more preferably about 50%, more preferably about 75% and even more preferably about 100% of the bacterial infection is reduced due to the administration of the compounds and compositions. A reduction in the infection is determined by such parameters as reduced white blood cell count, reduced fever, reduced inflammation, reduced number of bacteria, or reduction in other indicators of bacterial infection. To increase the percentage of bacterial infection reduction, the dosage can increase to the most effective level that remains non-toxic to the subject.

The compositions and compounds disclosed herein can be used in the same manner as antibiotics and antimicrobials. Uses of antibiotics and antimicrobials are well established in the art. One example of their use includes treatment of animals. When needed, the disclosed compounds can be administered to the animal via injection or through feed or water, usually with the professional guidance of a veterinarian or nutritionist. They are delivered to animals either individually or in groups, depending on the circumstances such as disease severity and animal species. Treatment and care of the entire herd or flock may be necessary if all animals are of similar immune status and all are exposed to the same disease-causing microorganism.

Another example of a use for the compositions and compounds includes reducing a microbial infection of an aquatic animal, comprising the steps of selecting an aquatic animal having a microbial infection, providing an antimicrobial solution comprising a compound as disclosed, chelating agents such as EDTA, TRIENE, adding a pH buffering agent to the solution and adjusting the pH thereof to a value of between about 7.0 and about 9.0, immersing the aquatic animal in the solution and leaving the aquatic animal therein for a period that is effective to reduce the microbial burden of the animal, removing the aquatic animal from the solution and returning the animal to water not containing the solution. The immersion of the aquatic animal in the solution containing the EDTA, a compound as disclosed, and TRIENE and pH buffering agent may be repeated until the microbial burden of the animal is eliminated. (U.S. Pat. No. 6,518,252).

Other uses of the compositions and compounds disclosed herein include, but are not limited to, dental treatments and purification of water (this can include municipal water, sewage treatment systems, potable and non-potable water supplies, and hatcheries, for example).

5. Kits

The compositions described above as well as other compositions and materials can be packaged together in any suitable combination as a kit useful for performing, or aiding in the performance of, the disclosed method. It is useful if the kit components in a given kit are designed and adapted for use together in the disclosed method.

EXAMPLES

Figure 1B:
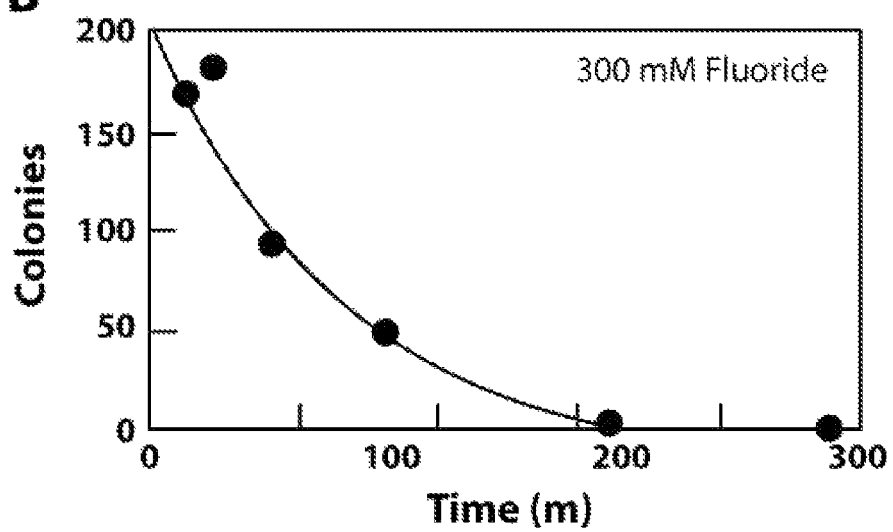
Figures 2A, 2B, 2C, 2D:
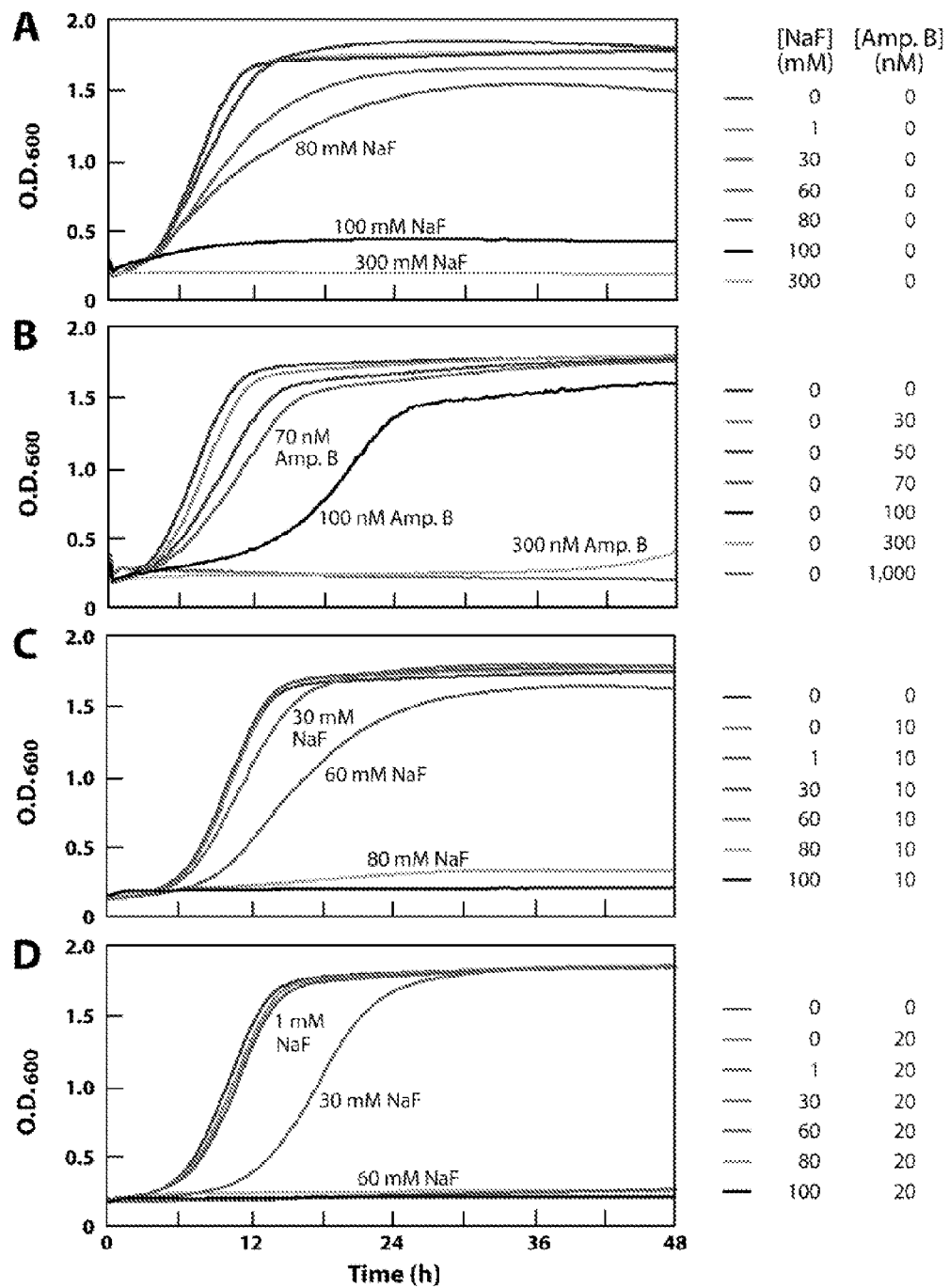
FIG. 2. (A) Fluoride inhibition of *S. cereviciae* growth in liquid culture over 48 hours. (B) Amphotericin B inhibition of *S. cereviciae* growth. (C), (D) Synergistic inhibition of *S. cereviciae* growth by a combination of fluoride and 10 or 20 nM amphotericin B, respectively.
Figures 3A, 3B, 3C, 3D:
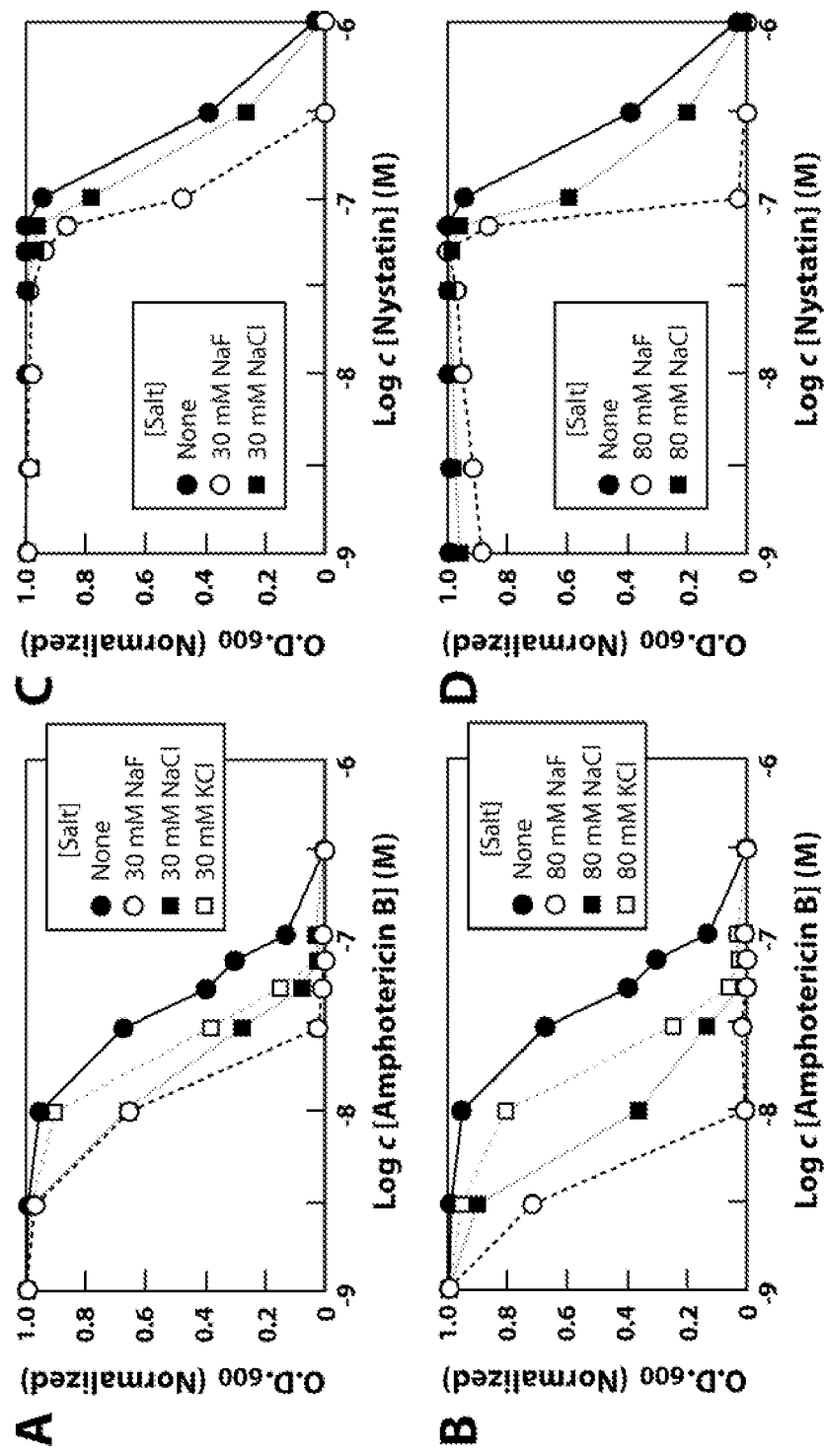
FIG. 3. (A) Effect of 30 mM fluoride or other ions on amphotericin B inhibition of *S. cereveciae* growth. Experiments were conducted as described for the data in FIG. 2, and data points (normalized to the maximum O.D.$_{600}$ value recorded for each culture) reflect 9 h incubations at 30° C. with shaking. (B) Effect of 80 mM fluoride or other ions on amphotericin B inhibition of *S. cereviciae* growth. (C), (D) Effects of 30 mM or 80 mM fluoride or other ions on nystatin inhibition of *S. cerevisiae* growth.
Figure 4:
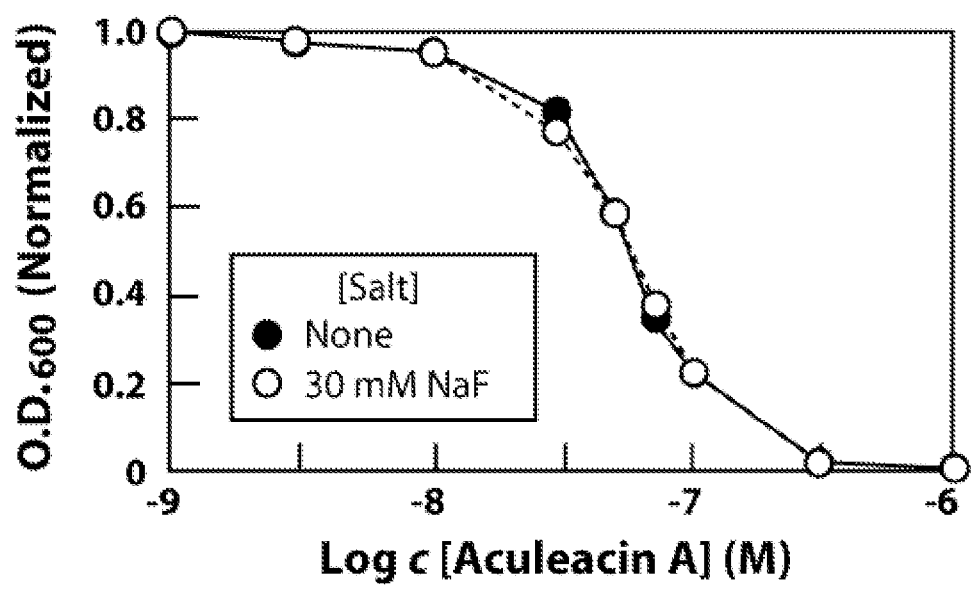
FIG. 4 shows the lack of an effect of 30 mM fluoride on aculeacin A inhibition of *S. cereveciae* growth. Experiments were conducted as described for the data in FIG. 3.

1. Example 1—Fluoride Toxicity, Fluoride Transporters and Compounds that Promote Fluoride Uptake CrcB proteins are most likely fluoride transporters. The fungal expression of crcB and the subsequent ejection of fluorides from cells is a major mechanism for how these organisms overcome fluoride toxicity. To assess whether fluoride simply halts fungal growth (fungistatic) or kills fungal cells (fungicidal), a culture of *Saccharomyces cereviciae* and added 300 mM fluoride to the medium was prepared. Samples of this mixture were taken at various times, plated, and the number of resulting colonies were recorded (FIG. 1). Cells experience a rapid loss of viability, and a 160 minute incubation results in near complete killing of the cells in the culture. Therefore, compounds that facilitate the uptake and/or retention of fluoride, or otherwise inhibit the fluoride toxicity mitigation responses of fungi, also function as fungicidal compounds when used in combination with fluoride.

Fluoride is a small chemical entity with fungicidal activity when present at high concentrations in cells, see Figure. 1. Compounds, such as a permeabilizing agent, that disrupt the integrity of cell membranes could interact synergistically with fluoride to more effectively inhibit fungal growth. Specifically, the addition of fluoride to a fungal growth medium containing a concentration of such an antifungal agent below its typical MIC (minimum inhibitory concentration) improves its MIC value. Likewise, these antifungal compounds lower the concentration of fluoride needed to inhibit fungal growth.

i. Imipramine as a Blocker of a Fluoride Transporter
Compound: Imipramine
Structure:

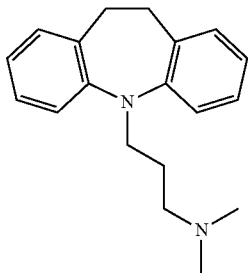

a. Assay

Fluoride riboswitch fused to a beta-galactosidase reporter gene. Construct is present in *E. coli* cells and cells are exposed to concentrations of sodium fluoride and imipramine (x-axis) as noted in FIG. 10.

b. Results

Figure 10:
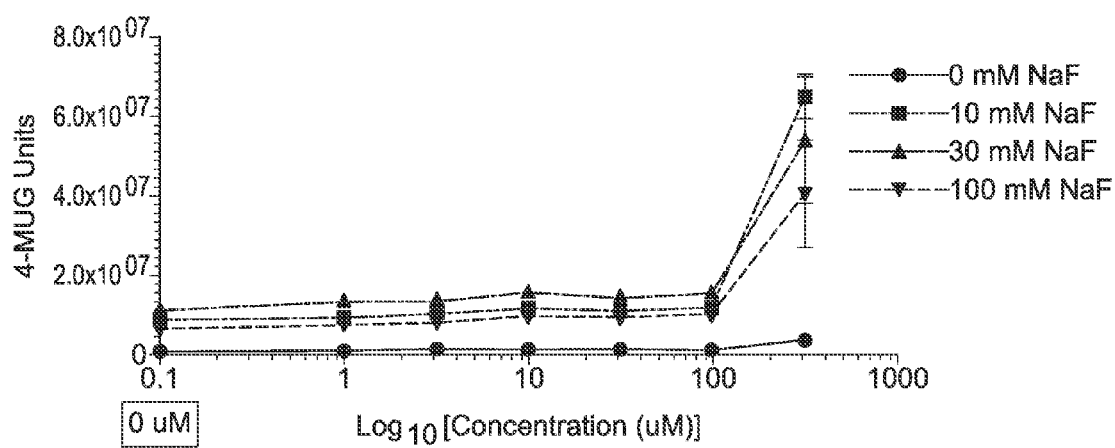
FIG. 10 shows the effect of a fluoride transporter, Imipramine, with fluoride.
Figures 11A, 11B, 11C:
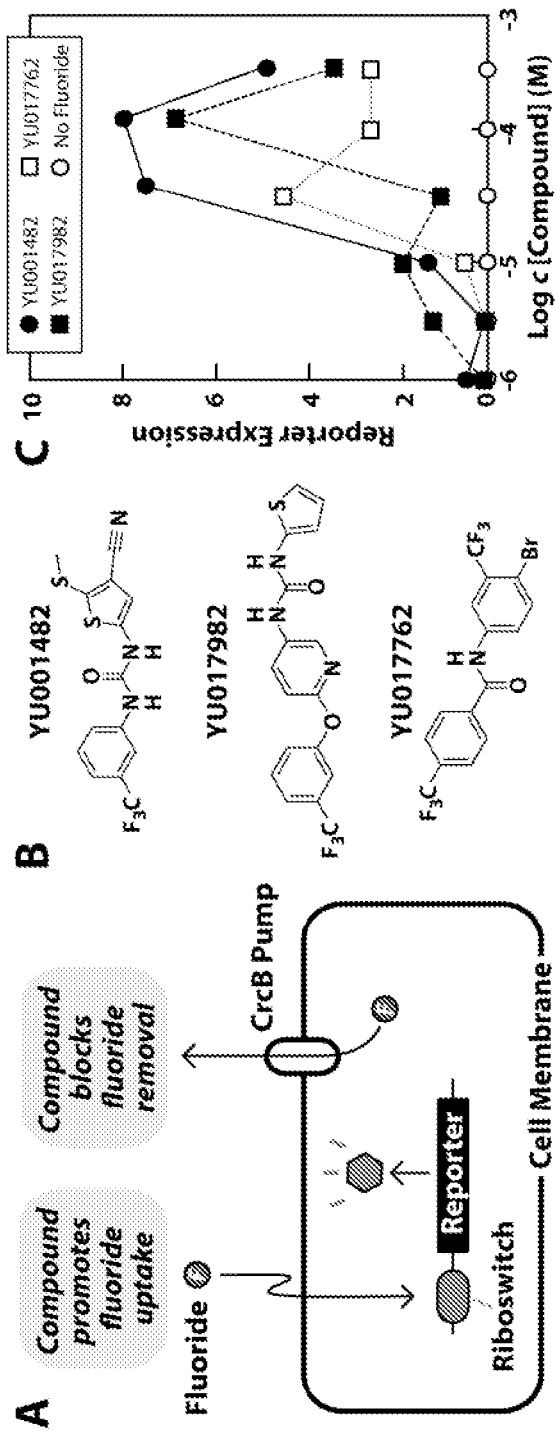
FIG. 11. (A) Two general mechanisms of action (shaded boxes) for compounds that increase fluoride ion concentration in cells equipped with the fluoride riboswitch-reporter fusion construct. (B) Examples of hit compounds identified by HTP screening. (C) Reporter activity of three hit compounds examine in *E. coli* grown at 30 mM fluoride. Reporter expression values (Fluorescence Units×10$^8$) were corrected for the value in the absence of hit compound. Lower values at high compound concentrations also correspond to lower cell growth, possibly due to the toxic effects of increased fluoride concentrations in cells.

At 330 μM imipramine, cells exhibit increased expression of the reporter gene as detected by fluorescence using the enzyme substrate 4-MUG, see FIG. 10. This level of reporter gene expression with imipramine is substantially reduced when the same riboswitch-reporter fusion construct is used in *E. coli* cells lacking the gene to express the fluoride transporter protein CrcB. These results indicate that imipramine (a previously known transporter inhibitor blocks the crcB fluoride transporter.

ii. Compounds that Promote Fluoride Uptake

An in vivo fluoride concentration sensor system based on the fluoride riboswitch from *B. cereus* was developed (a close relative of *Bacillus anthracis*). The riboswitch from the crcB gene was fused to a β-galactosidase reporter gene to create a riboswitch-reporter construct that increases reporter enzyme activity with increasing cellular concentration of fluoride. This construct was transfected into *E. coli* cells and used to conduct an initial HTP screen that yielded dozens of hits. Each hit is expected to trigger expression by increasing the concentration of fluoride in cells, either by enhancing uptake or by reducing pump-mediated removal (FIG. 11A). Additional validation experiments need to be conducted to confirm this conclusion for each hit.

Examples of hits (FIG. 11B) and their effects on reporter gene expression (FIG. 11C) indicate that a diversity of chemical structures indeed can trigger expression driven by a fluoride riboswitch. These preliminary findings need to be confirmed and additional compounds with similar activities need to be assessed.

2. Example 2—Synergistic Effect of Small Antimicrobial Agents and Permeabilizing Agents The synergistic effect of a small antimicrobial agent and a permeabilizing agent was shown by growth curve analyses of *S. cereviciae* in the presence or absence of various concentrations of sodium fluoride and amphotericin B, see FIG. 2. Amphotericin B, a permeabilizing agent, is a prominent member of the polyene class of antifungal agents and therefore allows fluoride to more readily gain entry into cells. Fluoride alone only marginally affects *S. cereviciae* growth when present at 30 mM in liquid medium under the specified growth conditions, see FIG. 2A. The addition of >100 mM fluoride was required to completely inhibit fungal growth over a 48-hour culture. In the absence of fluoride, concentrations of amphotericin B ranging from 30 to 70 nM only marginally delay near full growth of the *S. cereviciae* culture, while 300 nM of amphotericin B was required to almost completely inhibit growth over 48 hours, see FIG. 2B.

To assess the effects of the combination of fluoride and amphotericin B, *S. cereviciae* cultures were exposed to compositions containing 10 nM of amphotericin B to a range of fluoride concentrations. 10 nM amphotericin B has almost no effect on cell growth when used alone. However, when used in combination with fluoride its causes a dramatic increase in the growth-inhibition effects of fluoride, see FIG. 2C. The toxicity of fluoride is further enhanced by doubling the concentration of amphotericin B to 20 nM, see FIG. 2D. For example, 60 mM fluoride has only a modest effect on fungal growth when tested alone, but causes complete inhibition of growth when combined with a concentration of amphotericin B (20 nM) that otherwise has almost no growth inhibition effect on *S. cereviciae.*

The synergistic activity between fluoride and polyene class compounds is made further evident when fluoride concentrations are held constant and antifungal compound concentrations are varied, see FIG. 3. For example, amphotericin B undergoes an improvement in MIC for *S. cereviciae* of approximately 10 fold when 30 mM fluoride is added to liquid medium, see FIG. 3A. Moreover, 80 mM fluoride alone only lengthens the time to near full culture growth by two fold, but improves the MIC of amphotericin B by ~30 fold, see FIG. 3B. It was also observed that KCl and NaCl improve the MIC values of amphotericin B when tested at 30 mM and 80 mM, indicating that they too may exploit the membrane-destabilization mechanism to adversely affect fungal growth. However, KCl and NaCl are consistently less effective than NaF at causing fungal growth inhibition. Similar anion enhancement effects are observed for 30 mM (FIG. 3C) and 80 mM (FIG. 3D) fluoride when combined with nystatin, a related polyene class member.

Fluoride did not improve the function of compounds from most other antifungal agent classes examined. For example, aculeacin A, a member of an antifungal class that inhibits cell wall biosynthesis (Hector, R. F. Clin. Rev. Microbiol. 1993, 6, 1), is not affected at all by the presence of 30 mM fluoride (FIG. 4). Likewise, representatives of other classes either failed to be improved by the addition of fluoride (itraconazole) or did not significantly inhibit *S. cereviciae* growth (tolnaftate, terbinafine) under the assay conditions (data not shown). These findings indicate that the synergistic effects observed for fluoride (and to a lesser extent other ions) are likely to broadly improve the function of only those antifungal compounds, such as a permeabilizing agent, that compromise the ability of cell membranes to act as a barrier to ions.

Figures 5A, 5B, 5C, 5D:
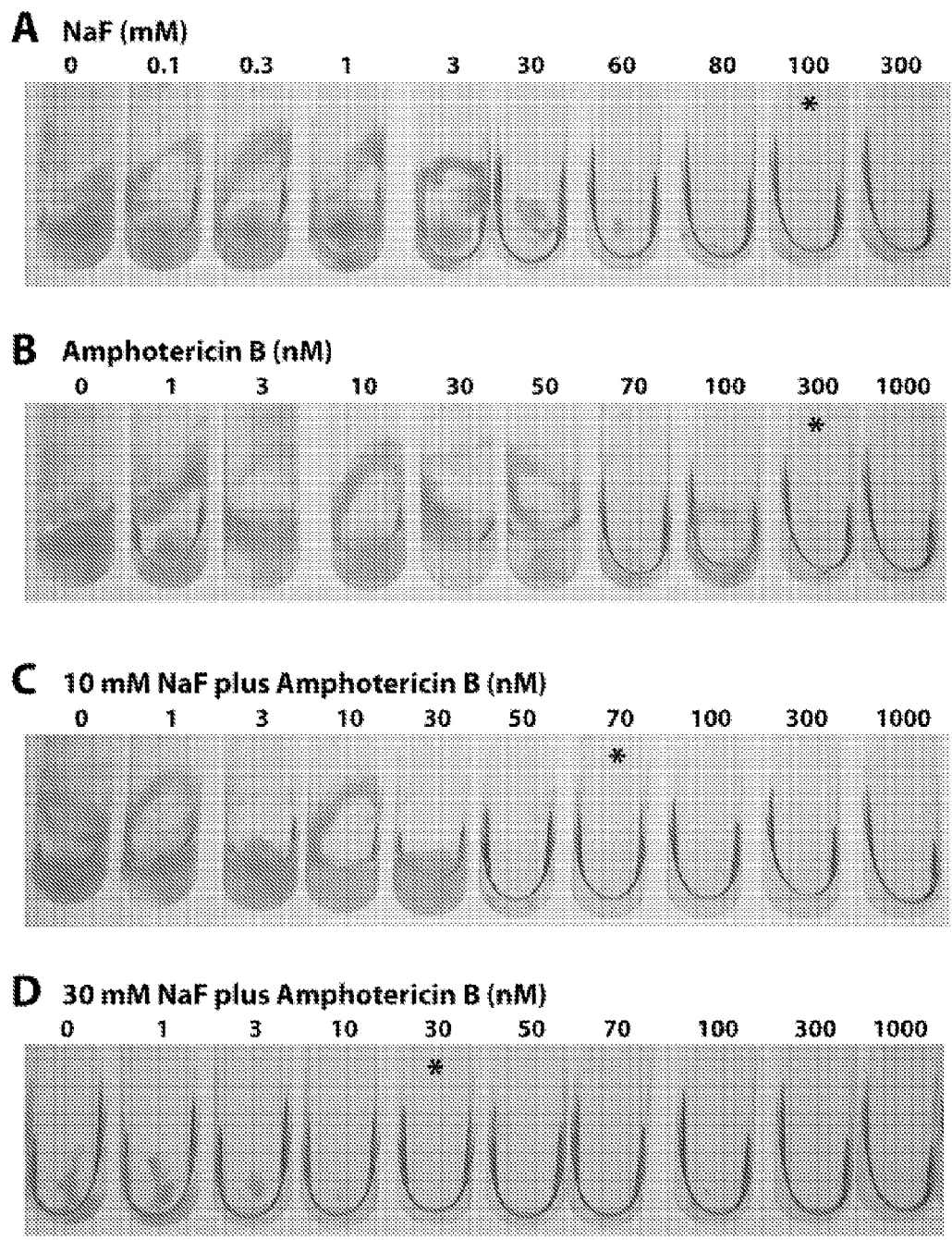
FIG. 5(A) shows the fluoride inhibition of *N. crassa* growth in liquid culture after incubation for 24 h. The asterisks denote tubes with the lowest concentration of fluoride or amphotericin B where little or no cell growth is visible. (B) Amphotericin B inhibition of *N. crassa* growth. (C), (D) Synergistic inhibition of *N. crassa* growth by a combination of amphotericin B and 10 or 30 mM fluoride, respectively.

Polyene antifungal compounds have broad efficacy against numerous species. A synergy between fluoride and certain antifungal compounds was observed in fungi, such as *S. cereviciae. Neurospora crassa* is a filamentous fungus and antifungal activity assays were conducted by visually examining liquid media cultures incubated with either fluoride, amphotericin B, or both, see FIG. 5. When tested independently, fluoride concentrations of greater than 80 mM were required to completely prevent *N. crassa* growth, see FIG. 5A, and a concentration of greater than 300 nM amphotericin B was required to prevent growth, see FIG. 5B. In contrast, combining 10 mM or 30 mM fluoride with amphotericin B reduces the MIC for the antifungal compound by at least 4 fold (FIG. 5C) and 10 fold (FIG. 5D), respectively. Similar synergy in the actions of fluoride and amphotericin B was also evident with another filamentous fungal species *Aspergillus nidulans* (FIGS. 8A-8D).

Figures 6A, 6B, 6C:
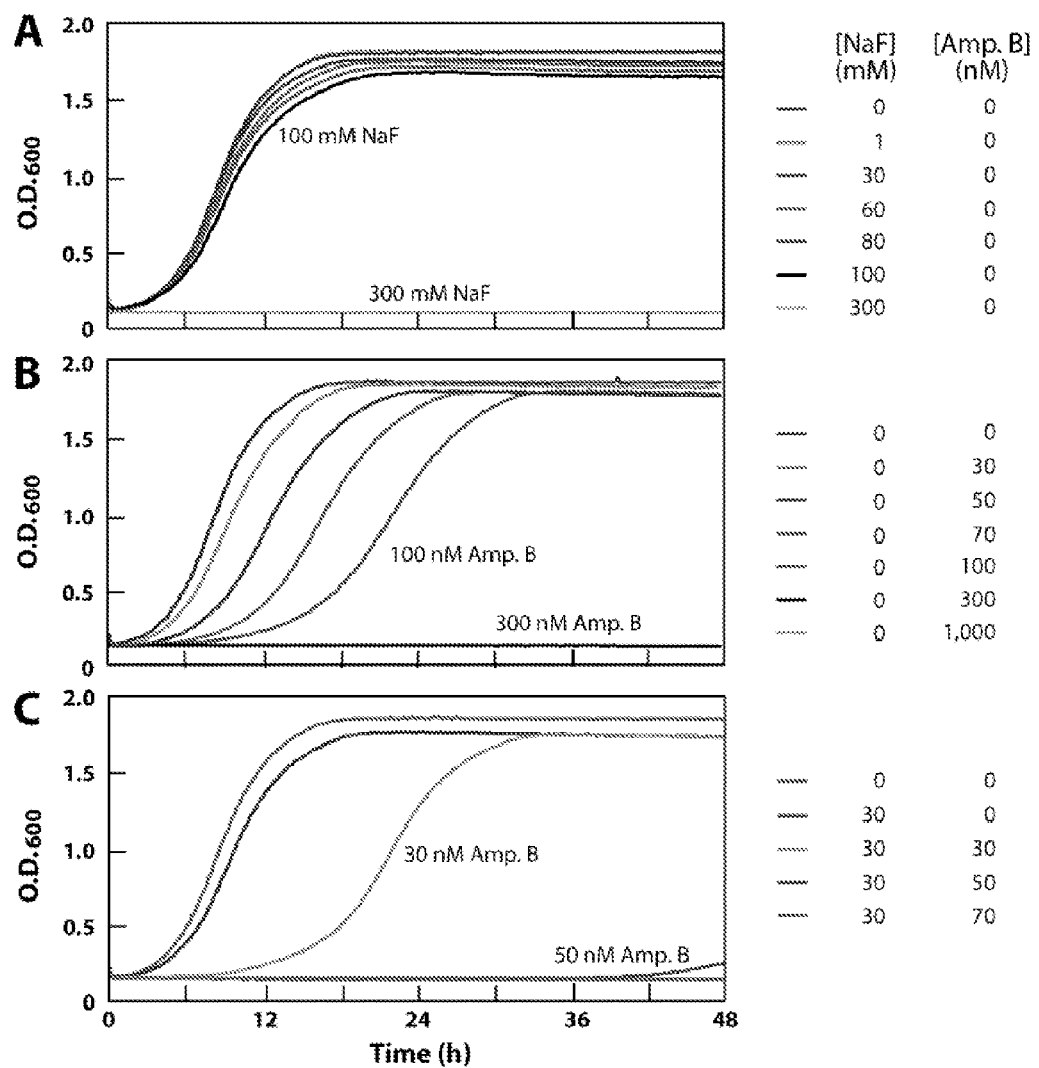
FIG. 6. (A) Fluoride inhibition of *C. albicans* growth in liquid culture over 48 hours. (B) Amphotericin B inhibition of *C. albicans* growth. (C) Synergistic inhibition of *C. albicans* growth by a combination of 30 mM fluoride and amphotericin B.

Fluoride also improves the MIC values for amphotericin B with the fungal pathogen *Candida albicans*, FIG. 6. Among the four fungal species to be examined in this study, *C. albicans* exhibited the greatest resistance to fluoride-mediated growth inhibition. When tested alone, 300 mM fluoride completely prevented growth in liquid medium after 48 hours, whereas 100 mM fluoride had only a modest inhibitory effect, see FIG. 6A. Increasing concentrations of amphotericin B ranging from 30 to 300 nM progressively inhibited cell growth, with the MIC for the compound falling somewhere between 100 and 300 nM, see FIG. 6B. However, this MIC for amphotericin B improved to ~50 nM when the medium is supplemented with only 30 mM fluoride, see FIG. 6C.

Figure 7:
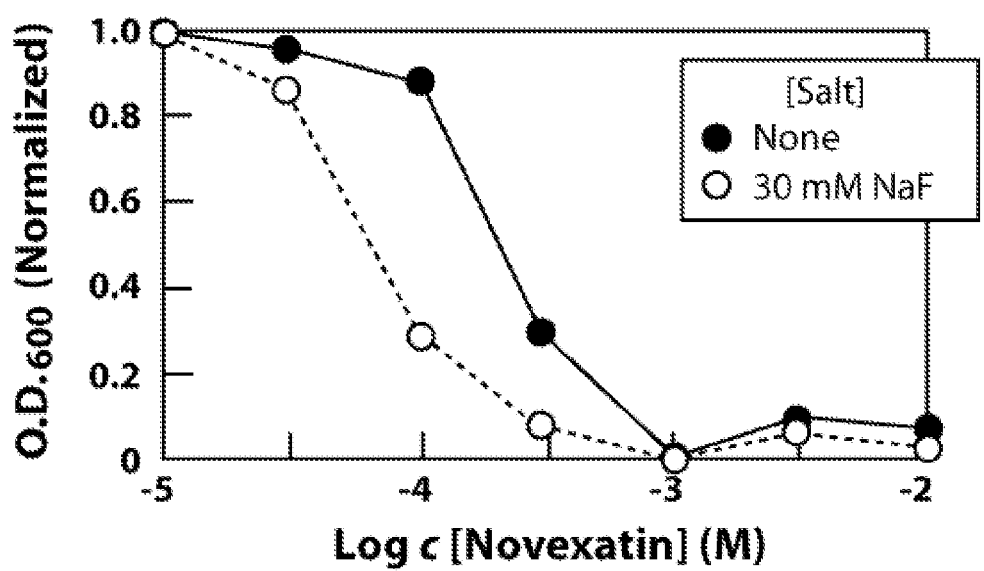
FIG. 7 shows the improvement in MIC of *S. cereviciae* with Novexatin® at 26.25 h upon the addition of 30 mM NaF.
Figure 8A:
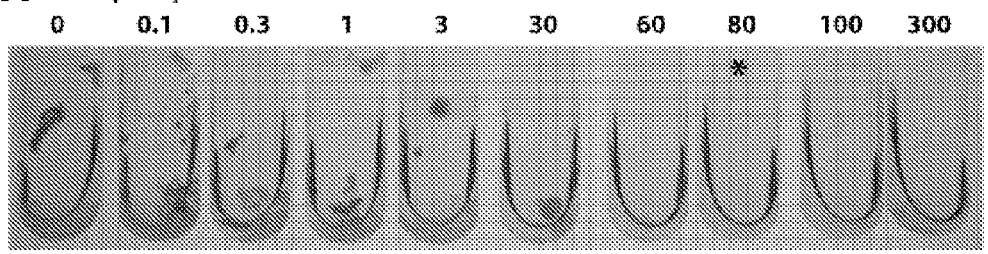
FIG. 8 shows the synergistic effects of fluoride and Amp. B on the growth of *A. nidulans* cells. (A) Fluoride inhibition of *A. nidulans* growth in liquid culture after incubation for 24 h. The asterisks denote tubes with the lowest concentration of fluoride or amphotericin B where little or no cell growth is visible. (B) Amphotericin B inhibition of *A. nidulans* growth. (C), (D) Synergistic inhibition of *A. nidulans* growth by a combination of amphotericin B and 10 or 30 mM fluoride, respectively.
Figure 8B:
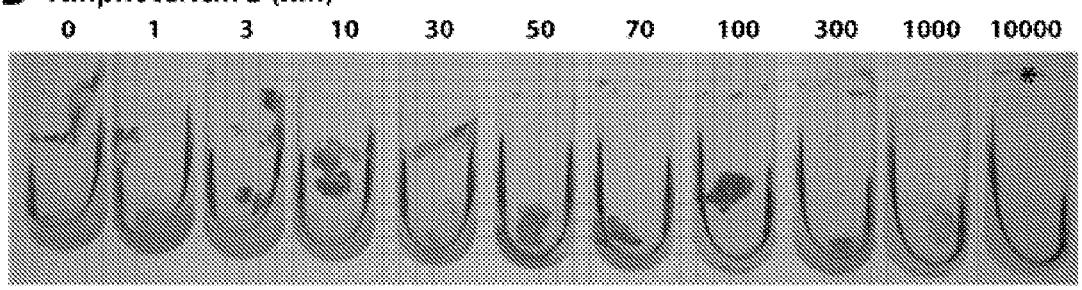
Figure 8C:
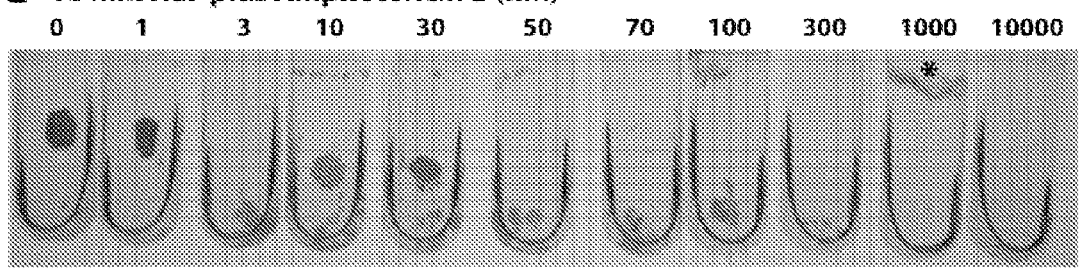
Figure 8D:
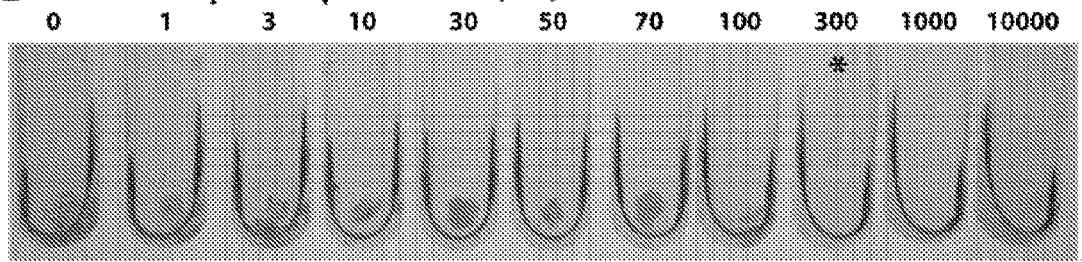
Figure 9A:
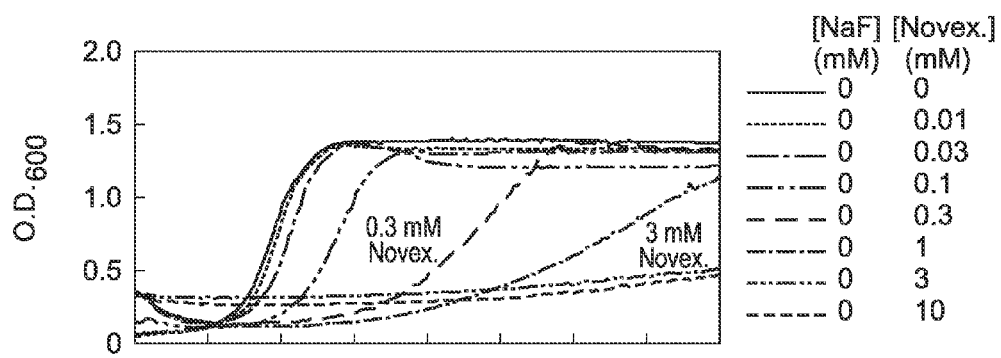
FIG. 9 shows the synergistic effects of fluoride and Novexatin® (Novex-®) on the growth of *S. cereviciae*. Yeast growth is depicted for various concentrations of Novexatin® in the absence (A) or presence (B) of 30 mM fluoride. Lower O.D.$_{600}$ compared to previous experiments is due to the use of smaller volumes of culture. Higher initial O.D.$_{600}$ values for the 1, 3 and 10 mM Novexatin® concentrations are due to compound insolubility.
Figure 9B:
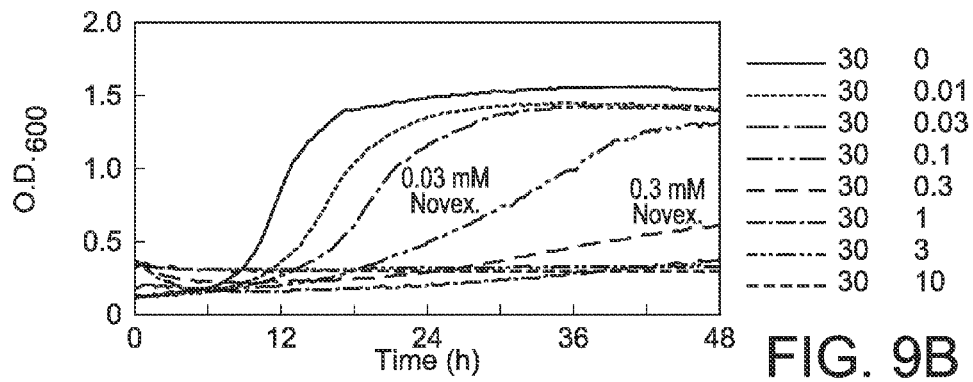

Another antifungal compound that has been proposed to function by destabilizing or permeabilize membranes is a circular hepta-arginine peptide with the commercial name NOVEXATIN® (NP213; NovaBiotics, Aberdeen, UK) (O'Neil, D. U.S. Pat. No. 7,847,059 B2, 2010; Duncan, V. M. S. et al., ICAAC 49th Conference Proceedings, 2009, Poster Abstract F1-852; Bamford, C. A. et al., ICAAC 49th Conference Proceedings, 2009, Poster Abstract F1-854). Growth curves conducted with *S. cereviciae* (FIGS. 9A and 9B) confirm that NOVEXATIN® has MIC values for fungi that are high relative to most commercial antifungal compounds. Under our culture conditions, 3 mM NOVEXATIN® was needed to almost completely prevent fungal growth over 48 hours. Solubility of NOVEXATIN® at millimolar concentrations becomes an issue, which made precise determination of MIC values problematic. Regardless, a greater than 3-fold improvement in MIC was obtained for NOVEXATIN® when combined with 30 mM fluoride. A similar result was obtained when evaluating cultures that were allowed to incubate for approximately 24 hours, see FIG. 7. These results are consistent with the mechanism of membrane destabilization by NOVEXATIN®.

The results are consistent with that the toxic effects of fluoride on fungi can be augmented by the use of compounds that facilitate the uptake of fluoride from growth media. The positive results with antifungal compounds that destabilize membranes also indicates that compounds affecting other processes involved in fluoride toxicity resistance would similarly increase the antimicrobial effects of fluoride. For example, compounds that affect bacterial membrane integrity or fluoride toxicity resistance systems also would enhance the antibacterial effects of anions, such as fluoride.

Fluoride has been known for many decades to broadly inhibit the growth of fungi (Nickerson, W. J. et al., Am. J. Botany 1952, 39, 669-679; Treshow, M. Mycologia 1965, 57, 216; Leslie, R. et al., Trans. British Mycol. Soc. 1972, 58, 351), albeit the concentrations of this anion required to achieve this effect are very high. The compositions and methods described herein reduce the requirement for high fluoride or of its more potent salts (Flisfisch, S.; Meyer, J.; Meurman, J. H.; Waltimo, T. Oral Diseases 2008, 14, 296) to achieve fungicidal activity.

Membrane destabilization by various compounds permit increased uptake of other antimicrobial chemical entities. Agents that are small and have little inherent toxicity to humans might be most advantageously applied in combination with membrane destabilizing antimicrobial compounds. Fluoride is routinely and daily applied to human tissues in the form of oral healthcare products such as over-the-counter (approximately 70 mM fluoride) or prescription (approximately 250 mM fluoride) toothpastes and mouthwashes. Furthermore, the relative selectivity of compounds such as amphotericin B and nystatin for fungal cells indicates that antifungal formulations containing both a polyene drug and low millimolar amounts of fluoride can offer a safe and effective topical treatment for certain fungal infections.

i. Materials and Methods a. Reagents

Sodium fluoride, adenine hydrochloride, thiamin hydrochloride, amphotericin B, nystatin, itraconazole, tolnaftate, terbinafine, and aculeacin A were purchased from Sigma-Aldrich. Novexatin® (cyclic hepta-arginine) was prepared by and purchased from Selleck Chemicals (Houston, Tex.). The compound was generated by solid-phase peptide synthesis and the mass of the HPLC-purified (C18 column) product was confirmed by mass spectroscopy. Bacto Yeast Extract, Bacto Proteose Peptone and Bacto Agar were purchased from BD Biosciences. Glucose (dextrose) was purchased from J. T. Baker.

b. Fungal Strains

*S. cerevisiae* MYH500 was obtained as a gift from Dr. Mark Hochstrasser (Yale University). The Fungal Genetics Stock Center was the source of *N. crassa* (FGSC #2225) and *A. nidulans* (ATCC number 38163, Glasgow wild-type). *C. albicans* (SC5314; ATCC number MYA-2876) was obtained from ATCC.

ii. Protocols a. Fungicidal Fluoride Assays: *S. cerevisiae*

Model Organism: *Saccharomyces cerevisiae* MYH500 [Genotype: his3-del200, leu2-3, ura3-52, lys2-801, trp1-1, gal2]

Medium: YPD (liquid and solid)

YPD Preparation (Liquid):

| | |
|---|---|
| Bacto yeast extract | 10 g |
| Bacto peptone | 20 g |
| $H_2O$ | 950 mL |
| [Autoclave, and then add filter-sterilized . . .] | |
| 1% adenine | 2 mL |
| 40% glucose | 50 mL |

YPD Preparation (Solid):

| | |
|---|---|
| Bacto yeast extract | 10 g |
| Bacto protease peptone | 20 g |
| $H_2O$ | 950 mL |
| Glucose | 20 g |

-continued

| | |
|---|---|
| 2% Bacto Agar | 20 g |
| [Autoclave, and then add filter-sterilized . . .] | |
| 1% adenine | 2 mL |

After addition of adenine and while the medium is still in liquid form, make plates (100×15 mm petri dishes) with 15 ml of agar media added to each.

Methods:
1. Pick an isolated yeast colony (*S. cerevisiae* MYH500) from a plate, inoculate into 2 mL YPD medium (liquid) in a 14 mL snap-cap tube and grow for 12 h at 30° C. on a shaker (200 rpm).
2. Dilute 20 μL of the culture into 2 mL medium and mix. Remove a 20 μL aliquot and transfer to 2 mL YPD medium with 300 mM NaF. Grow at 30° C. on a shaker (200 rpm) for 10, 20, 40, 80, 160 and 240 m.
3. At each time point, transfer 100 μL culture to an agar plate and distribute.
4. Incubate plates at 30° C. for about 24 hours.
5. Count the resulting colonies.

b. Growth Assays for Antifungal Compounds Combined with Fluoride: *S. cerevisiae*

Model Organism: *Saccharomyces cerevisiae* MYH500 [Genotype: his3-del200, leu2-3, ura3-52, lys2-801, trp1-1, gal2]

Medium: YPD (liquid)

Methods:
1. Pick an isolated yeast colony (*S. cerevisiae* MYH500) from a plate, inoculate into 2 mL YPD medium in a 14 mL snap-cap tube and grow for 12 h at 30° C. on a shaker (200 rpm). The O.D.$_{600}$ of the culture should be approximately 1.30.
2. Two growth methods are used. (i) If culturing cells in 14 mL snap-cap tubes, dilute the cells 1:3 (1 vol. of 12 hr cell culture plus 2 vol. medium). Then, inoculate 2 mL YPD medium with 20 μL of 1/3 diluted cells (1% inoculation). Incubate at 30° C. with 200 rpm shaking for 9 hours before measuring O.D. (ii) For growth curve measurements, culture cells in a honeycomb 2 plate (Oy Growth Curves Ab Ltd) with 400 μL of medium inoculated with 8 μL of 1:6 diluted cells (1% inoculation). Culture for 24 hrs at 30° C., measuring O.D.$_{600}$ every 15 m without shaking in a Bioscreen C MBR instrument (Oy Growth Curves Ab Ltd).
3. Supplement a fungicide and/or fluoride in the culture as necessary for each experiment.

c. Growth Assays for Antifungal Compounds Combined with Fluoride: *N. crassa*

Model Organism: *Neurospora crassa* (FGSC #2225) [Genotype: *N. crassa*, A]

Medium: Minimal medium
Minimal Medium Preparation:

| | |
|---|---|
| 50X Vogel's | 2 mL |
| Glucose | 2 g |
| H$_2$O | 100 mL |
| [Autoclave] | |

Methods:
1. Recover *N. crassa* on a slant with minimal medium at 25° C. for 5-6 days to grow spores.
2. Re-suspend two loops of spores in 2 mL minimal medium.
3. Inoculate 20 μL into 2 mL minimal medium in an autoclaved 16×150 mm glass tube with cap.
4. Supplement a fungicide and/or fluoride in the culture as necessary for each experiment.
5. Grow for 24 h at 25° C. on a shaker (200 rpm).

d. Growth Assays for Antifungal Compounds Combined with Fluoride: *A. nidulans*

Model Organism: *Aspergillus nidulans* (ATCC number 38163, Glasgow wild-type)

Medium: Minimal medium (plus thiamin)
Minimal Medium (Plus Thiamin) Preparation:

| | |
|---|---|
| 50X Vogel's | 2 mL |
| Glucose | 2 g |
| 1% thiamin | 0.1 mL |
| H$_2$O | 100 mL |
| [Autoclave] | |

(A) Methods:
1. Recover *A. nidulans* on a slant with minimal medium plus thiamin at 30° C. for 5-6 days to grow spores.
2. Re-suspend spores by adding 2 mL minimal medium plus thiamin to the slant, scraping with metal loop.
3. Inoculate 20 μL into 2 mL minimal medium plus thiamin in an autoclaved 16×150 mm glass tube with cap.
4. Supplement a fungicide and/or fluoride in the culture as necessary for each experiment.
5. Grow for 24 h at 30° C. on a shaker (200 rpm).

e. Growth Assays for Amphotericin B Combined with Fluoride: *C. albicans*

Organism: *Candida albicans* (SC5314; ATCC number MYA-2876)

Medium: YPD (liquid)

Methods:
1. Pick an isolated *C. albicans* yeast colony from a plate, inoculate into 2 mL YPD medium in a 17 mL screw-cap tube and grow for 12 h at 28° C. on a shaker (200 rpm). The O.D.$_{600}$ of the culture should be approximately 3.6.
2. Two growth methods were used. (i) If culturing cells in 17 ml screw-cap tubes, dilute the cells 1:5 (1 volume of 12 hr cell culture plus 4 volumes of medium). Inoculate 2 mL YPD medium with 20 μL of 1-to-5 diluted cells (1% inoculation). Incubate at 28° C. and 200 rpm for 9 hours before measuring O.D. (ii) For growth curve measurements, culture cells in a honeycomb 2 plate with 400 μL of medium inoculated with 8 μL of 1-to-10 diluted cells (1% inoculation). Culture for 48 hrs at 28° C., measuring OD$_{600}$ every 15 m without shaking in the Bioscreen C MBR instrument.
3. Supplement a fungicide and/or fluoride in the culture as necessary for each experiment.

Precautions:
A. All samples and disposable materials (tips, tubes, wipes, cuvettes, etc.) should be contained in a biohazard bag and the materials should be autoclaved before disposal. Remaining liquid culture solutions are low in total volume, and therefore do not require a different method for disposal.
B. Experimenter must wear latex gloves or a suitable replacement, lab coat, and protective eye wear that are dedicated to the project.
C. Equipment (shaker, growth curve machine, spectrophotometer) should be reserved for use with this project until the experiment is completed.

f. Growth Assays for Novexatin Combined with Fluoride: *S. cerevisiae*

Model Organism: *Saccharomyces cerevisiae* MYH500 [Genotype: his3-del200, leu2-3, ura3-52, lys2-801, trp1-1, gal2]

Medium: YPD (liquid)

Methods:
1. Pick an isolated yeast colony (*S. cerevisiae* MYH500) from a plate, inoculate into 2 mL YPD medium in a 14 mL snap-cap tube and grow for 12 h at 30° C. on a shaker (200 rpm). The O.D.$_{600}$ of the culture should be approximately 1.30.
2. For growth curve measurements, culture cells in a honeycomb 2 plate with 80 µL of medium (final volume) inoculated with 2 µL of 1:12 diluted cells. Culture for 48 hrs at 30° C., measuring O.D.$_{600}$ every 15 m without shaking in the Bioscreen C MBR instrument.
3. Supplement a fungicide and/or fluoride in the culture as necessary for each experiment.

Note that high concentrations (1 to 10 mM) of Novexatin® in the medium appeared to precipitate, and yield high O.D.$_{600}$ values for several hours after set-up.

Unless defined otherwise, all technical and scientific terms used herein have the same meanings as commonly understood by one of skill in the art to which the disclosed invention belongs. Publications cited herein and the materials for which they are cited are specifically incorporated by reference.

Those skilled in the art will recognize, or be able to ascertain using no more than routine experimentation, many equivalents to the specific embodiments of the invention described herein. Such equivalents are intended to be encompassed by the following claims.

REFERENCES

1. Dismukes, W. E. *Clin. Infect. Disease.* 2006, 42, 1289.
2. Pitman, S.; Drew, R. H.; Perfect, J. R. *Expert Opin. Emerg. Drugs* 2011, 16, 559.
3. Ghannoum, M. A.; Rice, L. B. Clin. *Microbiol. Rev.* 1999, p. 501.
4. Kaur, I. P.; Kakkar, S. *Expert Opin. Drug Deliv.* 2010, 7, 1303.
5. Weinberg, Z.; Wang, J. X.; Bogue, J.; Yang, J.; Corbino, K.; Moy, R. H.; Breaker, R. R. *Genome Biol.* 2010, 11, R31.
6. Baker, J. L.; Sudarsan, N.; Weinberg, Z.; Roth, A.; Stockbridge, R. B.; Breaker, R. R. *Science* 2012, 335 (6065):233-5.
7. Mandal, M.; Breaker, R. R. Nature Rev. *Mol. Cell Biol.* 2004, 5, 451.
8. Roth, A.; Breaker, R. R. *Annu. Rev. Biochem.* 2009, 78, 305.
9. Smith, A. M.; Fuchs, R. T.; Grundy, F. J.; Henkin, T. M. *RNA Biol.* 2010, 7, 104-110.
10. Rapp, M.; Granseth, E.; Seppälä, S.; von Heijne, G. *Nat. Struct. Mol. Biol.* 2006, 13, 112.
11. Finn, R. D. et al., *Nucleic Acids Res.* 2010, 38, D211.Holt, R. J. *Ann. N.Y. Acad. Sci.* 1974, 235, 469.
12. De Kruijff, B.; Demel, R. A. *Biochim. Biophys. Acta* 1974, 339, 57.
13. Kerridge, D. In: The Eukaryotic Cell, Gooday, G. W.; Lloyd, D., Trinci, A. P. J., Eds; Cambridge University Press, 1980, p. 103.
14. Hector, R. F. *Clin. Rev. Microbiol.* 1993, 6, 1.
15. O'Neil, D. U.S. Pat. No. 7,847,059 B2, 2010.
16. Duncan, V. M. S.; Robertson, J.; Turvey, L.; Miller, L.; Charrier, C.; Bamford, C. A.; Stewart, C. S.; Mercer, D. K.; O'Neil, D. A. *ICAAC 49th Conference Proceedings,* 2009, Poster Abstract F1-852.
17. Bamford, C. A.; Galloway, D. B.; O'Neil, D. A. *ICAAC 49th Conference Proceedings,* 2009, Poster Abstract F1-854.
18. Nickerson, W. J.; Chung, C. W. *Am. J. Botany* 1952, 39, 669-679.
19. Treshow, M. *Mycologia* 1965, 57, 216.
20. Leslie, R.; Parbery, D. *J. Trans. British Mycol. Soc.* 1972, 58, 351.
21. Flisfisch, S.; Meyer, J.; Meurman, J. H.; Waltimo, T. *Oral Diseases* 2008, 14, 296.

We claim:

1. An antimicrobial composition comprising an effective amount of a small antimicrobial agent in combination with an effective amount of one or more further agents, wherein the small antimicrobial agent and the one or more further agents are together effective to reduce growth or viability of microbial cells, wherein the one or more further agents comprise a first antimicrobial agent, wherein the one or more further agents increase the cellular uptake, retention, or both, of the small antimicrobial agent in the microbial cells, wherein the first antimicrobial agent increases the retention of the small antimicrobial agent, wherein the reduction in growth or viability of the microbial cells is more than the additive reduction achieved by using each agent alone, wherein the first antimicrobial agent has the structure

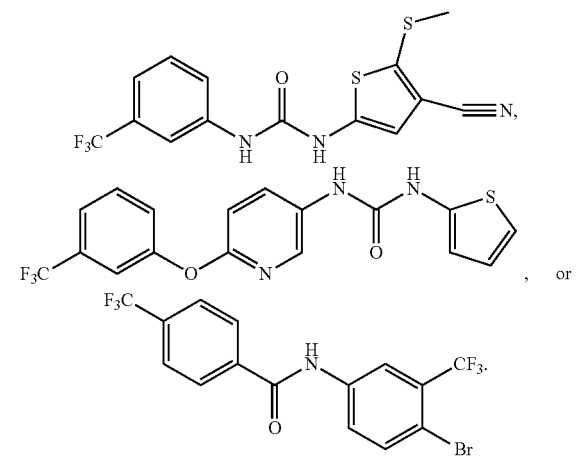

, or

2. The composition of claim 1, wherein the small antimicrobial agent is a small antifungal agent.

3. The composition of claim 1, wherein the small antimicrobial agent is an anion or a pharmaceutically acceptable salt thereof.

4. The composition of claim 1, wherein the small antimicrobial agent is selected from the group consisting of fluoride, chloride, bromide, and iodine.

5. The composition of claim 1, wherein the small antimicrobial agent is selected from the group consisting of fluoride salts, chloride salts, bromide salts, and iodine salts.

6. The composition of claim 1, wherein the small antimicrobial agent is fluoride or a pharmaceutically acceptable salt thereof.

7. The composition of claim 1 further comprising a carrier, wherein the carrier comprises a cream, paste, fluid, coating, paint, spray, detergent, or a combination.

8. The composition of claim 1 further comprising a carrier, wherein the carrier comprises antimicrobial cream, antimicrobial paste, antimicrobial fluid, antimicrobial coating, antimicrobial paint, antimicrobial spray, antimicrobial detergent, antimicrobial soap, mouthwash, skinwash, nasal wash, toothpaste, toothwash, dish detergent, laundry detergent, dishwasher detergent, nasal spray, mouth spray, throat spray, skin spray, douche fluid, enema fluid, wound cleanser, wound covering, eyewash, shampoo, facial wash, facial cream, or facial soap.

9. A method of treating a microbial condition comprising, administering to a subject in need thereof the composition of claim 1 in an amount effective to reduce growth or viability of microbial cells.

10. The method of claim 9, wherein the small antimicrobial agent is an antifungal agent.

11. The method of claim 9, wherein the small antimicrobial agent is an anion or a pharmaceutically acceptable salt thereof.

12. The method of claim 9, wherein the small antimicrobial agent is selected from the group consisting of fluoride, chloride, bromide, iodine.

13. The method of claim 9, wherein the small antimicrobial agent is selected from the group consisting of fluoride salts, chloride salts, bromide salts, and iodine salts.

14. The method of claim 9, wherein the small antimicrobial agent is fluoride or a salt thereof.

15. The method of claim 9, wherein the composition is administered as a cream, paste, fluid, coating, paint, spray, detergent, or a combination.

16. The method of claim 9, wherein the one or more further agents further comprise a permeabilizing agent, wherein the permeabilizing agent increases the cellular uptake of the small antimicrobial agent.

17. The method of claim 16, wherein the permeabilizing agent is not an ion channel-forming peptide or protein.

18. The method of claim 16, wherein the permeabilizing agent is a polyene macrolide or NP213.

19. The method of claim 18, wherein the polyene is selected from the group consisting of amphotericin B, amphotericin B deoxycholate, liposomal amphotericin B, amphotericin B lipid complex, amphotec, candidin, candidoin, candidinin, mycoheptin, nystatin, polyfungin, aureofacin, vacidin, trichomycin, candicidin, and pimaricin.

20. The method of claim 19, wherein the polyene is amphotericin B.

21. An antimicrobial composition comprising an effective amount of a small antimicrobial agent in combination with an effective amount of a permeabilizing agent and an effective amount of a first antimicrobial agent, wherein the small antimicrobial agent, the permeabilizing agent, and the first antimicrobial agents are together effective to reduce growth or viability of microbial cells,
wherein the permeabilizing agent increases the cellular uptake of the small antimicrobial agent, wherein the first antimicrobial agent increases the retention of the small antimicrobial agent,
wherein reduction in microbial growth or viability is more than the additive reduction achieved by using each agent alone, and
wherein the first antimicrobial agent has the structure

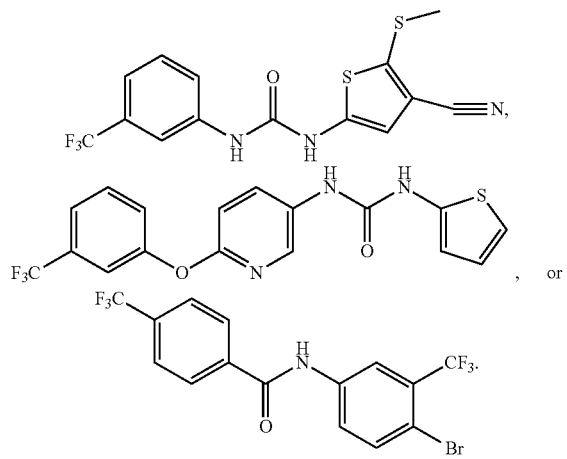

22. The composition of claim 21, wherein the permeabilizing agent is a polyene macrolide or NP213.

23. The composition of claim 22, wherein the polyene is selected from the group consisting of amphotericin B, amphotericin B deoxycholate, liposomal amphotericin B, amphotericin B lipid complex, amphotec candidin, candidoin, candidinin, mycoheptin, nystatin, polyfungin, aureofacin, vacidin, trichomycin, candicidin, and pimaricin.

24. The composition of claim 23, wherein the polyene is amphotericin B.

25. A method of treating a microbial condition comprising, administering to a subject in need thereof the composition according to claim 21.

* * * * *